(12) United States Patent
Godara et al.

(10) Patent No.: US 8,951,249 B2
(45) Date of Patent: *Feb. 10, 2015

(54) ELECTROSURGICAL DEVICE WITH DISCONTINUOUS FLOW DENSITY

(75) Inventors: Neil Godara, Mississauga (CA); Wesley Dawkins, Toronto (CA); Taylor Hillier, Georgetown (CA); Mark Leung, Toronto (CA)

(73) Assignee: Avent Inc., Alpharetta, GA (US)

( * ) Notice: Subject to any disclaimer, the term of this patent is extended or adjusted under 35 U.S.C. 154(b) by 2013 days.

This patent is subject to a terminal disclaimer.

(21) Appl. No.: 11/356,706

(22) Filed: Feb. 17, 2006

(65) Prior Publication Data

US 2006/0217705 A1    Sep. 28, 2006

Related U.S. Application Data

(63) Continuation-in-part of application No. 11/280,604, filed on Nov. 15, 2005, now Pat. No. 7,819,869.

(60) Provisional application No. 60/593,839, filed on Feb. 17, 2005, provisional application No. 60/594,787, filed on May 5, 2005, provisional application No. 60/595,426, filed on Jul. 4, 2005, provisional application No. 60/595,559, filed on Jul. 14, 2005, provisional application No. 60/595,560, filed on Jul. 14, 2005.

(51) Int. Cl.
*A61B 18/14* (2006.01)
*A61B 18/00* (2006.01)

(52) U.S. Cl.
CPC ........... *A61B 18/1482* (2013.01); *A61B 18/148* (2013.01); *A61B 2018/00083* (2013.01); *A61B 2018/00196* (2013.01); *A61B 2018/00434* (2013.01); *A61B 2018/0044* (2013.01); *A61B 2018/1475* (2013.01); *A61B 2018/1497* (2013.01)
USPC .......................................................... 606/41

(58) Field of Classification Search
CPC ............... A61B 18/12; A61B 18/1402; A61B 18/1477; A61B 18/1482; A61B 2018/00083; A61B 2018/00339; A61B 2018/1425; A61B 2018/1467
USPC ......................................... 606/41, 42, 48–50
See application file for complete search history.

(56) References Cited

U.S. PATENT DOCUMENTS 4,041,931 A    8/1977  Elliott et al.
4,202,349 A    5/1980  Jones (Continued)

FOREIGN PATENT DOCUMENTS

EP    0547772 A1    6/1993
EP    0642800 A1    3/1995

(Continued)

OTHER PUBLICATIONS

Kline MT, Yin W. "Radiofrequency techniques in clinical practice". Interventional Pain Management. 243-I☐☐290 (2001).*

(Continued)

*Primary Examiner* — Ronald Hupczey, Jr.
(74) *Attorney, Agent, or Firm* — Dority & Manning, P.A.

(57) ABSTRACT

An electrosurgical device comprising a means for impeding flow for delivering energy to a region of tissue is described. In addition, a method of treating the sacroiliac region of a patient's body by delivering energy is also described. The method includes the steps of inserting a probe into a target site within the sacroiliac region of a patient's body and delivering energy to the probe to treat tissue within the target site.

22 Claims, 9 Drawing Sheets

(56) References Cited

U.S. PATENT DOCUMENTS

| | | | |
|---|---|---|---|
| 4,257,429 A | 3/1981 | Dickhudt et al. | |
| 4,419,095 A | 12/1983 | Nebergall et al. | |
| 4,447,239 A | 5/1984 | Krutten | |
| 4,548,207 A | 10/1985 | Reimels | |
| 4,612,934 A | 9/1986 | Borkan | |
| 4,657,024 A | 4/1987 | Coneys | |
| 5,191,900 A | 3/1993 | Mishra | |
| 5,209,749 A | 5/1993 | Buelna | |
| 5,342,343 A | 8/1994 | Kitaoka et al. | |
| 5,342,357 A | 8/1994 | Nardella | |
| 5,397,338 A | 3/1995 | Grey et al. | |
| 5,429,597 A | 7/1995 | DeMello et al. | |
| 5,429,617 A | 7/1995 | Hammersmark et al. | |
| 5,433,739 A | 7/1995 | Sluijter et al. | |
| 5,545,193 A * | 8/1996 | Fleischman et al. | 607/99 |
| 5,571,147 A | 11/1996 | Sluijter et al. | |
| 5,693,043 A | 12/1997 | Kittrell et al. | |
| 5,759,174 A | 6/1998 | Fischell et al. | |
| 5,766,171 A | 6/1998 | Silvestrini | |
| 5,776,092 A | 7/1998 | Farin | |
| 5,779,642 A | 7/1998 | Nightengale | |
| 5,800,428 A | 9/1998 | Nelson et al. | |
| 5,855,577 A | 1/1999 | Murphy-Chutorian et al. | |
| 5,895,386 A | 4/1999 | Odell | |
| 5,951,546 A | 9/1999 | Lorentzen | |
| 6,002,964 A | 12/1999 | Feler et al. | |
| 6,056,743 A | 5/2000 | Ellis et al. | |
| 6,102,886 A | 8/2000 | Lundquist | |
| 6,104,957 A | 8/2000 | Alo et al. | |
| 6,106,524 A * | 8/2000 | Eggers et al. | 606/50 |
| 6,126,654 A | 10/2000 | Giba et al. | |
| 6,129,726 A | 10/2000 | Edwards | |
| 6,146,380 A | 11/2000 | Racz et al. | |
| 6,162,216 A | 12/2000 | Guziak et al. | |
| 6,176,857 B1 | 1/2001 | Ashley | |
| 6,186,147 B1 * | 2/2001 | Cobb | 128/898 |
| 6,197,021 B1 | 3/2001 | Panescu et al. | |
| 6,235,000 B1 | 5/2001 | Milo et al. | |
| 6,251,104 B1 | 6/2001 | Kesten et al. | |
| 6,277,112 B1 | 8/2001 | Underwood et al. | |
| 6,280,441 B1 | 8/2001 | Ryan | |
| 6,306,132 B1 | 10/2001 | Moorman et al. | |
| 6,315,790 B1 | 11/2001 | Gerberding et al. | |
| 6,355,033 B1 | 3/2002 | Moorman et al. | |
| 6,379,349 B1 * | 4/2002 | Muller et al. | 606/41 |
| 6,447,506 B1 | 9/2002 | Swanson et al. | |
| 6,464,723 B1 | 10/2002 | Callol | |
| 6,471,700 B1 | 10/2002 | Burbank et al. | |
| 6,478,783 B1 | 11/2002 | Moorehead | |
| 6,501,992 B1 | 12/2002 | Belden et al. | |
| 6,562,033 B2 | 5/2003 | Shah et al. | |
| 6,582,426 B2 | 6/2003 | Moorman et al. | |
| 6,620,156 B1 | 9/2003 | Garito | |
| 6,622,731 B2 | 9/2003 | Daniel et al. | |
| 6,726,684 B1 | 4/2004 | Woloszko | |
| 6,735,474 B1 | 5/2004 | Loeb et al. | |
| 6,757,565 B2 | 6/2004 | Sharkey | |
| 6,770,070 B1 | 8/2004 | Balbierz | |
| 6,773,446 B1 | 8/2004 | Dwyer et al. | |
| 6,780,181 B2 * | 8/2004 | Kroll et al. | 606/41 |
| 6,847,849 B2 | 1/2005 | Mamo et al. | |
| 6,893,421 B1 | 5/2005 | Larson et al. | |
| 6,902,526 B2 | 6/2005 | Katzman | |
| 6,932,811 B2 | 8/2005 | Hooven | |
| 6,966,902 B2 | 11/2005 | Tsugita et al. | |
| 6,974,454 B2 | 12/2005 | Hooven | |
| 6,974,457 B2 | 12/2005 | Gibson | |
| 7,063,698 B2 * | 6/2006 | Whayne et al. | 606/49 |
| 7,097,641 B1 | 8/2006 | Arless et al. | |
| 7,175,631 B2 | 2/2007 | Wilson et al. | |
| 7,462,178 B2 | 12/2008 | Woloszko et al. | |
| 2001/0000041 A1 | 3/2001 | Selmon et al. | |
| 2001/0027309 A1 | 10/2001 | Elsberry | |
| 2001/0056280 A1 | 12/2001 | Underwood | |
| 2002/0026127 A1 | 2/2002 | Balbierz | |
| 2002/0032440 A1 | 3/2002 | Hooven | |
| 2002/0049437 A1 | 4/2002 | Silvestrini | |
| 2002/0072739 A1 | 6/2002 | Lee | |
| 2002/0091384 A1 | 7/2002 | Godinho de Queiroz e Melo | |
| 2002/0103484 A1 | 8/2002 | Hooven | |
| 2002/0111617 A1 * | 8/2002 | Cosman et al. | 606/41 |
| 2002/0120260 A1 | 8/2002 | Morris et al. | |
| 2002/0147485 A1 | 10/2002 | Mamo et al. | |
| 2002/0193781 A1 | 12/2002 | Loeb | |
| 2003/0014047 A1 | 1/2003 | Woloszko | |
| 2003/0015707 A1 | 1/2003 | Bosco | |
| 2003/0023239 A1 | 1/2003 | Burbank et al. | |
| 2003/0032936 A1 | 2/2003 | Lederman | |
| 2003/0040742 A1 | 2/2003 | Underwood | |
| 2003/0093007 A1 | 5/2003 | Wood | |
| 2003/0100895 A1 | 5/2003 | Simpson et al. | |
| 2003/0109870 A1 | 6/2003 | Lee | |
| 2003/0120195 A1 | 6/2003 | Milo et al. | |
| 2003/0125729 A1 | 7/2003 | Hooven | |
| 2003/0153906 A1 | 8/2003 | Sharkey | |
| 2003/0158545 A1 | 8/2003 | Hovda et al. | |
| 2003/0212394 A1 | 11/2003 | Pearson et al. | |
| 2003/0212395 A1 | 11/2003 | Woloszko | |
| 2003/0233125 A1 | 12/2003 | Kaplan et al. | |
| 2004/0054366 A1 | 3/2004 | Davison | |
| 2004/0082942 A1 | 4/2004 | Katzman | |
| 2004/0106891 A1 | 6/2004 | Langan et al. | |
| 2004/0187875 A1 | 9/2004 | He et al. | |
| 2004/0199161 A1 | 10/2004 | Truckai et al. | |
| 2004/0215287 A1 | 10/2004 | Swoyer et al. | |
| 2004/0249373 A1 | 12/2004 | Gronemeyer et al. | |
| 2004/0267203 A1 | 12/2004 | Potter et al. | |
| 2004/0267254 A1 | 12/2004 | Manzo | |
| 2005/0033372 A1 | 2/2005 | Gerber et al. | |
| 2005/0049570 A1 | 3/2005 | Chin et al. | |
| 2005/0085806 A1 | 4/2005 | Auge, II et al. | |
| 2005/0096718 A1 | 5/2005 | Gerber et al. | |
| 2005/0177209 A1 | 8/2005 | Leung et al. | |
| 2005/0177211 A1 | 8/2005 | Leung et al. | |
| 2005/0187542 A1 | 8/2005 | Auge | |
| 2005/0240238 A1 | 10/2005 | Mamo et al. | |
| 2006/0020297 A1 | 1/2006 | Gerber et al. | |
| 2006/0025763 A1 | 2/2006 | Nelson et al. | |

FOREIGN PATENT DOCUMENTS

| | | |
|---|---|---|
| EP | 0651661 B1 | 6/2000 |
| EP | 0865768 A1 | 2/2003 |
| EP | 1344497 A1 | 9/2003 |
| WO | 81/03272 A1 | 11/1981 |
| WO | 94/02077 A2 | 2/1994 |
| WO | 9409560 A1 | 4/1994 |
| WO | 9422384 A1 | 10/1994 |
| WO | 9424948 A1 | 11/1994 |
| WO | 95/10320 A1 | 4/1995 |
| WO | 9510318 A1 | 4/1995 |
| WO | 9510327 A1 | 4/1995 |
| WO | 9521578 A1 | 8/1995 |
| WO | 9639967 A1 | 12/1996 |
| WO | 9706739 A2 | 2/1997 |
| WO | 9706855 A2 | 2/1997 |
| WO | 9724074 A1 | 7/1997 |
| WO | 98/19613 A1 | 5/1998 |
| WO | 9827879 A1 | 7/1998 |
| WO | 9831290 A1 | 7/1998 |
| WO | 9858747 A1 | 12/1998 |
| WO | 9942037 A1 | 8/1999 |
| WO | WO 99/43263 | 9/1999 |
| WO | WO 99/48548 | 9/1999 |
| WO | WO 01/45579 | 6/2001 |
| WO | 0167975 A3 | 9/2001 |
| WO | WO 01/70114 | 9/2001 |
| WO | 0174251 A3 | 10/2001 |
| WO | 2180724 A3 | 11/2001 |
| WO | 0245609 A2 | 6/2002 |
| WO | 03037162 A1 | 5/2003 |
| WO | 03065917 A1 | 8/2003 |
| WO | 03103522 A1 | 12/2003 |

(56) References Cited

OTHER PUBLICATIONS

Kline et al, "Radiofrequency Techniques in Clinical Practice", 2001, Interventional Pain Management, 243-290.*
Ahadian, "Pulsed Radiofrequency Neurotomy: Advances in Pain Medicine", 2004, 8(1), Current Pain Headache Report, 34-40.*
Cohen, Steven P. 'Sacroiliac Joint Pain: A Comprehensive Review of Anatomy, Diagnosis, and Treatment', Anesth Analg 2005;101:1440-53.
Buijs EJ, Kamphuis ET, Groen GJ. "Radiofrequency treatment of sacroiliac joint-related pain aimed at the first three sacral dorsal rami: A minimal approach". Pain Clinic. 16(2):139-146. 2004.
Jiang J., Xiao L.Z., Zheng H.S., Zhu H.Q. "Comparison between radiofrequency coagulation plus small needle knife and single method in treatment of sacrolumbar pain". Chinese Journal of Clinical Rehabilitation. 7(20):2844-2845. 2003.
Plancarte RS, Mayer-Rivera FJ. "Radiofrequency Procedures for Sacral and Pelvic Region Pain". Pain Practice. 2(3):248-249 (2002).
Fukui S, Nosaka S. "Succesful relief of hip joint pain by percutaneous radiofrequency nerve thermocoagulation in a patient with contraindications for hip arthroplasty". J Anesth. 15(3):173-175 (2001).
Cohen SP, Foster A. "Pulsed radiofrequency as a treatment for groin pain and orchialgia". Urology. 61(3):645 (2003).
Kawaguchi M, Hashizume K, Iwata T, Furuya H. "Percutaneous radiofrequency lesioning of sensory branches of the obturator and femoral nerves for the treatment of hip joint pain". Reg Anesth Pain Med. 26(6):576-581 (2001).
Akatov OV, Dreval ON. "Percutaneous radiofrequency destruction of the obturator nerve for treatment of pain caused by coxarthrosis". Stereotact Funct Neurosurg. 69(1-4 Pt 2): 278-280 (1997).
Ferrante FM, Aranda M, Delaney LR, Kim PS, King LF, Mannes AJ, Mardini IA, Roche EA "Radiofrequency sacroiliac joint denervation for sacroiliac syndrome". Reg Anesth Pain Med. 26(2):137-142 (2001).
Gopalani AF, Malik A, Simopolous T. "A novel technique for treating nonsurgical hip pain with radiofrequency lesioning of the sensory branches of the obturator and femoral nerves: a case report". Archives of Physical Medicine and Rehabilitation. 84(9): E23 (2003).
Pino CA, Hoeft MA, Hofsess C, Rathmell JP. "Morphologic analysis of bipolar radiofrequency lesions: implications for treatment of the sacroiliac joint". Reg Anesth Pain Med. 30(4):335-338 (2005).
Yin W, Willard F, Carreiro J, Dreyfuss P. "Sensory stimulation-guided sacroiliac joint radiofrequency neurotomy: technique based on neuroanatomy of the dorsal sacral plexus". Spine. 28(20):2419-2425 (2003).
Ahadian, FM. "Pulsed radiofrequency neurotomy: advances in pain medicine". Curr Pain Headache Rep. 8(1):34-40 (2004).
Gevargez A, Groenemeyer D, Schirp S, Braun M. "CT-guided percutaneous radiofrequency denervation of the sacroiliac joint". Eur Radiol. 12(6):1360-1365 (2002).
Anis N, Chawki N, Antoine K. "Use of radio-frequency ablation for the palliative treatment of sacral chordoma". AJNR. 25(9):1589-1591 (2004).
Conaghan P, Farouk R. "Sacral nerve stimulation can be successful in patients with ultrasound evidence of external anal sphincter disruption". Diseases of the Colon and Rectum. 48(8):1610-1614 (2005).
Kirsch DG, Ebb DH, Hernandez AH, Tarbell NJ. "Proton radiotherapy for Hodgkin's disease in the sacrum". Lancet Oncology. 6(7):532-533 (2005).
Leng WW, Chancellor MB. "How sacral nerve stimulation neuromodulation works". Urol Clin North Am. 32 (1):11-8 (2005).
Kirkham APS, Knight SL, Craggs MD, Casey ATM, Shah PJR. "Neuromodulation through sacral nerve roots 2 to 4 with a Finetech-Brindley sacral posterior and anterior root stimulator". Spinal Cord. 40(6):272-281 (2002).
Simon S. "Sacroiliac joint injection and low back pain". Interventional Pain Management. 535-539 (2001).
Kline MT, Yin W. "Radiofrequency techniques in clinical practice". Interventional Pain Management. 243-290 (2001).

Cole AJ, Dreyfuss P, Stratton SA. "The Sacroiliac Joint: A Functional Approach". Critical Reviews in Physical and Rehabilitation Medicine. 8(1&2):125-152 (1996).
Atlihan D, Tekdemir I, Ates Y, Elhan A. "Anatomy of the Anterior Sacroiliac Joint With Reference to Lumbosacral Nerves". Clinical Orthopaedics and Related Research. 376: 2360241 (2000).
Calvillo O, Skaribas I, Turnipseed J. "Anatomy and Pathophysiology of the Sacroiliac Joint". Current Review of Pain. 4:356-361 (2000).
Davies PW, Luthardt F, Statts PS. "Radiofrequency Treatment in the United States". Pain Practice. 2(3): 192-194 (2002).
Ebraheim NA, Lu J, Biyani A, Yeasting RA. "Anatomic Considerations for Posterior Approach to the Sacroiliac Joint". Spine. 21(23): 2709-2712 (1996).
Fortin JD, Washingtion WJ, Falco FJE. "Three Pathways between the Sacroiliac Joint and Neural Structures". Am J Neruoradiol. 20:1429-1434 (1999).
Fortin JD, Kissling RO, O'Connor BL, Vilensky JA. "Sacroiliac Joint Innervation and Pain". The American Journal of Orthopedics. 687-690, Dec. 1999.
Liguoro D, Viejo-Fuertes D, Midy D, Guerin J. "The Posterior Sacral Foramina: An Anatomical Study". J. Anat. 195:301-304 (1999).
Murata Y, Takahashi K, Yamagata M, Takahashi Y, Shimada Y, Moriya H. "Origin and pathway of sensory nerve fibers to the ventral and dorsal sides of the sacroiliac joint in rats". Journal of Orthopaedic Research. 19:379-383 (2001).
Prithvi Raj P, Erdine S. "The Current Status of the Practice of Radiofrequency in the World". Pain Practice. 2 (3):176-179 (2002).
Slipman CW, Whyte WS, Chow DW, Chou L, Lenrow D, Ellen M. "Sacroiliac Joint Syndrome". Pain Physician. 4(2):143-152 (2001).
Van Zundert J, Raj P, Erdine S, van Kleef M. "Application of Radiofrequency Treatment in Practical Pain Management: State of the art". Pain Practice. 2(3):269-278 (2002).
Dreyfuss P, Rogers CJ. "Radiofrequency Neurotomy of the Zygapophyseal and Sacroiliac Joints". Pain Proc. 2 (Chapter 32): 395-420 (2000).
Deer, T. "Injections for the Diagnosis and Treatment of Spinal Pain". American Society of Anesthesiologists 32 (Chapter 6):52-69 (2004).
Non Final Action for 1145-4, "Mailed on Jun. 20, 2008".
European Search Report for 1145-64, "Report Completed on Jan. 8, 2009 (EP 06705184.7)", 2009.
PCT IPRP for 1145-64, "Report Issued on Aug. 21, 2007 (PCT/CA2006/000229)", 2007.
PCT Written Opinion for 1145-64, "Completion Date of Opinion Mar. 29, 2006 (PCT/CA2006/000229)", 2006.
Cohen et al., "Lateral Branch Blocks as a Treatment for Sacroiliac Joint Pain: a Pilot Study", "Regional Anesthesia Pain Medicine", 2003, pp. 113-119, vol. 28, No. 2.
Office Action for U.S. Appl. No. 11/280,604 "Mailed on Dec. 8, 2009".
Office Action for U.S. Appl. No. 11/280,604, "Mailed on May 12, 2009".
Response to Office Action for U.S. Appl. No. 11/280,604, "Mailed on May 12, 2009" Mailed on Nov. 12, 2009.
Office Action for U.S. Appl. No. 11/381,783, "Mailed on Dec. 24, 2009".
Office Action for U.S. Appl. No. 11/534,907, "Mailed on May 28, 2009".
Response to Office Action for U.S. Appl. No. 11/534,907, "Mailed on May 28, 2009" Mailed on Oct. 28, 2009.
International Search Report (PCT/CA2006/001163)—7 pages.
International Search Report (PCT/CA2006/000229)—4 pages.
Bogduk et al., "Technical Limitations to the Efficacy of Radiofrequency Neurotomy for Spinal Pain", Neurosurgery 20(4):529-535, 1987.
Lord et al., "Percutaneous Radiofrequency Neurotomy in the Treatment of Cervical Zygapophyseal Joint Pain: A Caution", Neurosurgery 36(4):732-739, 1995.
Lau et al., "The Surgical Anatomy of Lumbar Medial Branch Neurotomy (Facet Denervation)", Pain Medicine 5(3):289-298, 2004.
Lord et al., "Percutaneous Radio-Frequency Neurotomy for Chronic Cervical Zygapophyseal-Joint Pain", New England Journal of Medicine 335(23):1721-1726, 1996.

(56) References Cited

OTHER PUBLICATIONS

Hooten et al., "Radiofrequency Neurotomy for Low Back Pain: Evidence-Based Procedural Guidelines", Pain Medicine 6(2):129-138, 2005.
Dreyfuss et al., "Lumbar Radiofrequency Neurotomy for Chronic Zygapophyseal Joint Pain: A Pilot Study Using Dual Medial Branch Blocks", ISIS Scientific Newsletter 3(2):13-30, 1999.
Baylis Medical Company, Inc., "Technology Notes—RF Lesion Size in Relation to Cannula Gauge", 2005.
Baylis Medical Company, Inc., "Baylis Medical Company—Radiopaque Cannula", 2005.
Curatolo et al., "Re: Nlemisto L., Kalso E., Malmivaara A., et al. Radiofrequency Denervation for Neck and Back Pain: A Systematic Review Within the Framework of the Cochrane Collaboration Back Review Group. Spine 2003, 28:1877-88", Spine 30(2):263-268, 2005.
Conaghan et al., "Sacral Nerve Stimulation can be Successful in Patients with Ultrasound Evidence of External Anal Sphincter Disruption", Diseases of the Colon & Rectum 38(8):1610-1614, Aug. 2005.
Valleylab—RF Pain Management System, Sep. 16, 2004, http://www.valleylab.com/static/pain/products-generator.html.

* cited by examiner

ELECTROSURGICAL DEVICE WITH
DISCONTINUOUS FLOW DENSITY

REFERENCES TO PARENT AND CO-PENDING
APPLICATIONS

This application claims priority from and is a continuation-in-part of U.S. patent application Ser. No. 11/280,604, filed Nov. 15, 2005 issued as U.S. Pat. No. 7,819,869 B2. In addition, this application claims the benefit of; U.S. provisional application No. 60/593,839, filed Feb. 17, 2005; U.S. provisional application No. 60/594,787, filed May 5, 2005; U.S. provisional application No. 60/595,426, filed JUL 4, 2005; U.S. provisional application No. 60/595,559, filed Jul. 14, 2005; and U.S. provisional application No. 60/595,560, filed Jul. 14, 2005. The aforementioned applications are all herein incorporated by reference.

TECHNICAL FIELD

The invention relates to a device and method for electrosurgery and more specifically for delivering energy or other matter to a region of a patient's body, including the sacroiliac region.

BACKGROUND OF THE ART

Ferrante et al. (Radiofrequency Sacroiliac Joint Denervation for Sacroiliac Syndrome; Regional Anaesthesia and Pain Medicine, Vol. 26, No. 2, pp. 137-142, March-April 2001, which is incorporated herein by reference) describe the creation of a strip lesion along the long axis of the posterior sacroiliac (SI) joint using Radiofrequency (RF) energy. Multiple probes are inserted along the joint margin and energy is delivered in a bipolar configuration. Such an approach requires multiple probe insertions and requires relatively precise probe placement in order to ensure adequate lesioning between the bipolar probes. Gevargez et al. (CT-Guided Percutaneous Radiofrequency Denervation of the Sacroiliac Joint; Eur Radiol (2002) 12:1360-1365, which is incorporated herein by reference) describe the creation of a strip lesion through the interosseous ligament surrounding the SI joint using RF energy. This approach, as detailed therein, requires multiple energy delivery and repositioning steps and does not allow for the creation of a lesion within the intra-articular space of the SI joint itself. Yin et al. (Sensory Stimulation-Guided Sacroiliac Joint Radiofrequency Neurotonomy: Technique based on Neuroanatomy of the Dorsal Sacral Plexus; (2003) SPINE, Vol. 28, No. 20, pp. 2419-2425, which is incorporated herein by reference) advocate lesioning a single branch of a sacral nerve as it exits the sacral foramina. The procedure described by Yin et al. may require a relatively skilled user due to the approach involved. In addition, the procedure detailed therein is time consuming as it involves multiple steps of probe re-positioning and neural stimulation in order to locate a single symptomatic nerve branch. Furthermore, this procedure does not allow for the creation of a strip lesion nor does it allow for the creation of a lesion within the SI joint. Thus, it would be desirable to have a procedure to treat the SI region using energy delivery that overcomes some or all of the limitations of the prior art.

BRIEF DESCRIPTION OF THE DRAWINGS

In order that the invention may be readily understood, embodiments of the invention are illustrated by way of examples in the accompanying drawings, in which.

DETAILED DESCRIPTION OF THE INVENTION

Definitions

As used herein, the term 'sacroiliac region' refers to the region of the patient's body comprising the sacrum and ilium and their articulation (including the sacroiliac joints) or associated ligaments.

Figure 1:
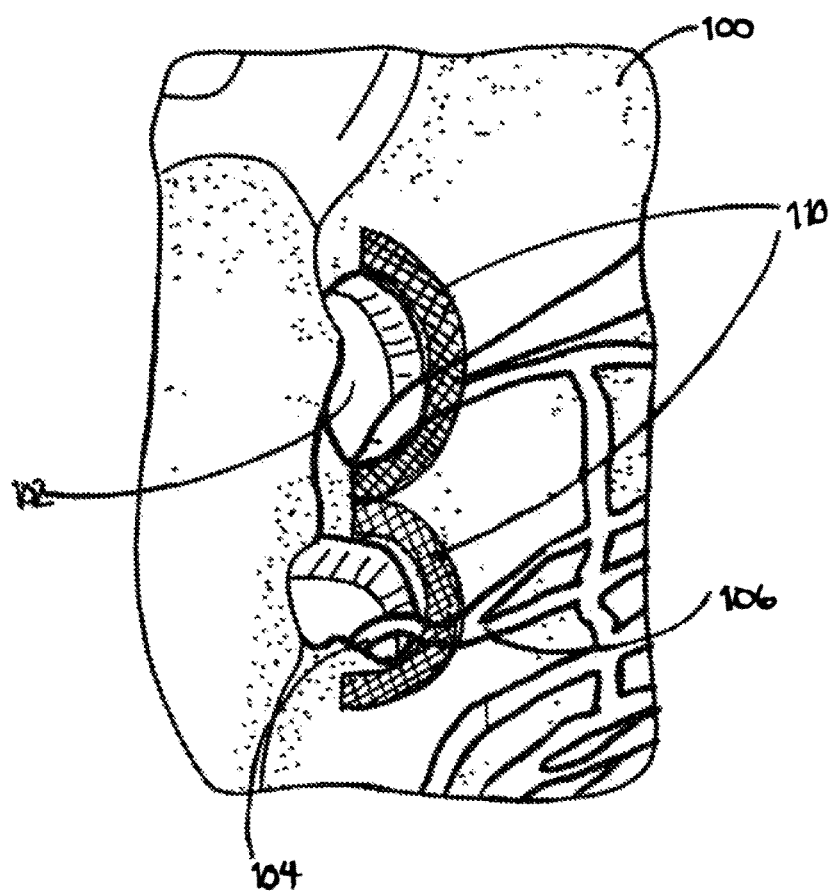
FIG. 1 is an illustration of the location of a sacral neural crescent in a patient's body.

Furthermore, as used herein, the 'sacral neural crescent' refers to an area lateral to each of the sacral foramina, through which the sacral nerves are believed to pass after exiting the foramina. On the dorsal right side of the sacrum, this window is from about 12 o'clock to about 6 o'clock in a clockwise direction, while on the dorsal left side of the sacrum the window is from about 6 o'clock to about 12 o'clock in a clockwise direction. Similar (but in the counter-clockwise direction) areas exist on the ventral side of the sacrum. The clock positions are referenced as if the foramen is viewed as a clock face, and the view is taken looking towards the sacrum. For reference, the 12 o'clock position of the clock face would be the most cephalad (towards the head) point of the foramen. FIG. 1 illustrates the position of two sacral neural crescents 110 on the dorsal right side of the sacrum 100. As can be seen, sacral nerves 104 and lateral branches 106 exit each of the sacral foramina 102 and pass through sacral neural crescents 110.

With specific reference now to the drawings in detail, it is stressed that the particulars shown are by way of example and for purposes of illustrative discussion of embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

Theory

Before explaining the structure in detail, it would be beneficial to illustrate a proposed theoretical concept underlying the function of the present invention. It is important to note that, although the theory being presented is currently believed to be true and accurate, the invention should not be limited by this or any other theory of operation. Rather, the breadth of the invention as will be presently described is intended to be limited only by the scope of the appended claims.

Current Density

The distribution of electrical current, i.e. the current density, arising from a radiating source such as an electrical conductor, is governed by several mathematical formulae, including Laplace's equation and Maxwell's equations. It is postulated that when an electrical conductor has regions of abrupt disruptions of conductivity (i.e. electrical discontinuity), these equations dictate that the current density in the vicinity of those regions will be higher than the current density found around other regions of the conductor. The term 'electrical discontinuity' may refer to any feature of a probe or other electrical device that may affect energy delivery from the surface of the probe to a surrounding environment. For example, an insulating material coating one or more regions of the active portion of a probe would result in an electrical discontinuity since energy delivery from the portion of the probe located around the insulating material is affected by the insulating material. Furthermore, notches or other surface irregularities in the active portion may also be considered to be electrical discontinuities, since they also may affect the delivery of energy from the surface of the probe to the surrounding environment. As another example, a distal end of a probe is considered to be an 'electrical discontinuity' if there is a disruption of energy delivery from the surface of the probe to the surrounding environment about the distal end of the probe.

This phenomenon may be referred to as an 'edge effect' and the regions of high current density may be referred to as 'hot spots'. So, for example, the current density in the vicinity of an interface between a conductive region and an electrically insulated region of an electrosurgical probe, may be higher than in the vicinity of the continuously conductive region of the probe, resulting in a localized 'hot spot' near the insulator/conductor interface. The temperature of tissue in the vicinity of a certain region of the probe may be proportional to the current density in that region.

A similar concept may be applied to devices that rely on fluid (rather than electrical current) flow or the flow of any other matter. Generally speaking, flow of any substance may be concentrated around edges of the device that serves as the source of the flow. In order to spread out the flow more effectively, especially when the flow source is long, it may be useful to interrupt the flow in some way along the length of the flow source, as has been described with respect to interruption of electrical current.

Apparatus

Structure

Figure 2:
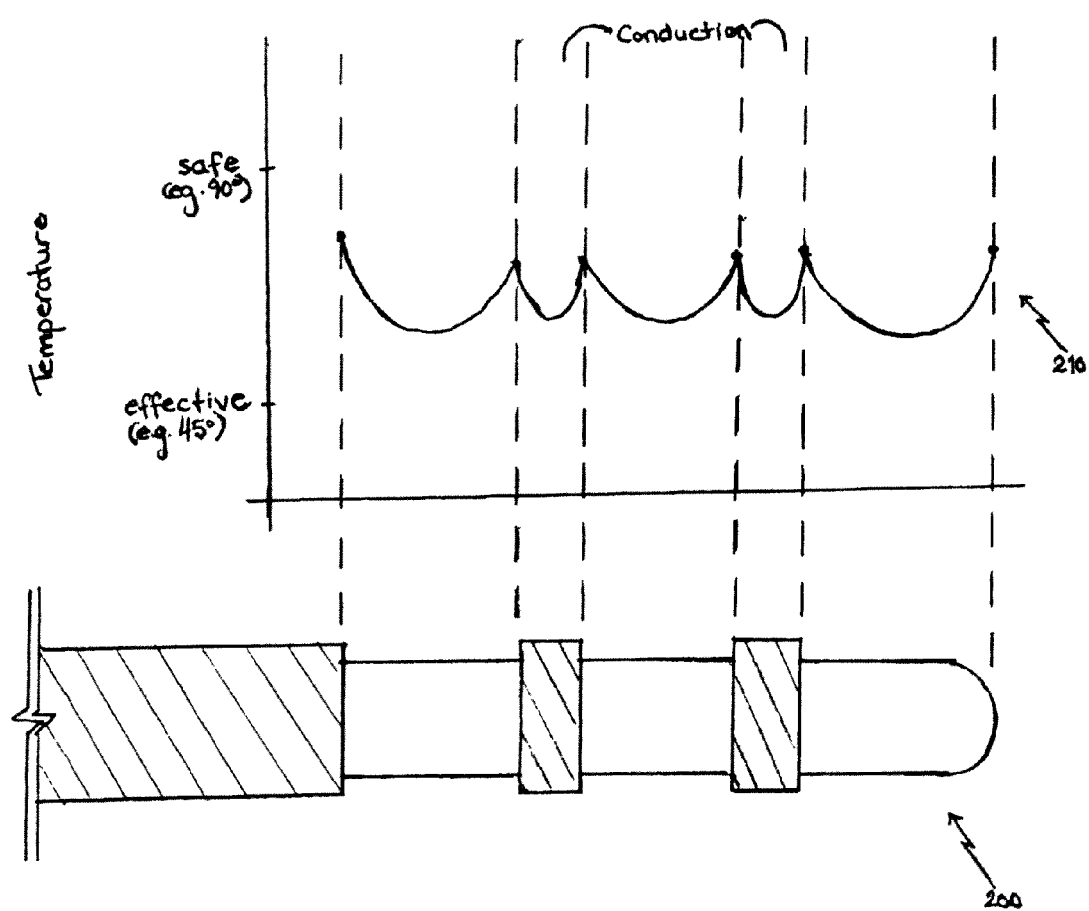
FIG. 2 shows an illustrative plot of an example of substantially homogeneous energy delivery.

According to one broad aspect of the present invention, a device is presented that is capable of creating a substantially homogeneous lesion in a patient's body. A substantially homogeneous lesion may refer to a continuous lesion that is created along the length of the active portion of a probe such that substantially all portions of tissue within the lesion area are at a temperature within a given range, where the range lies between an efficacious temperature (at the low end) and a safe temperature (at the high end). For example, if tissue must be heated to about 45 degrees Celsius in order to create a lesion effective to treat a tissue, while anything above about 90 degrees Celsius may be dangerous and damaging to the tissue, a substantially homogeneous lesion may be a continuous lesion within which substantially all portions of tissue have a temperature between about 45 to about 90 degrees Celsius. This concept is illustrated in FIG. 2, which shows a probe 200 and a plot 210 of a potential temperature distribution for tissue within a lesion created along the length of probe 200. In conjunction with the understanding of a substantially homogeneous lesion, the phrase 'Substantially homogeneous energy delivery' may be understood to describe the delivery of energy such that a substantially homogeneous lesion is created.

Figure 3:
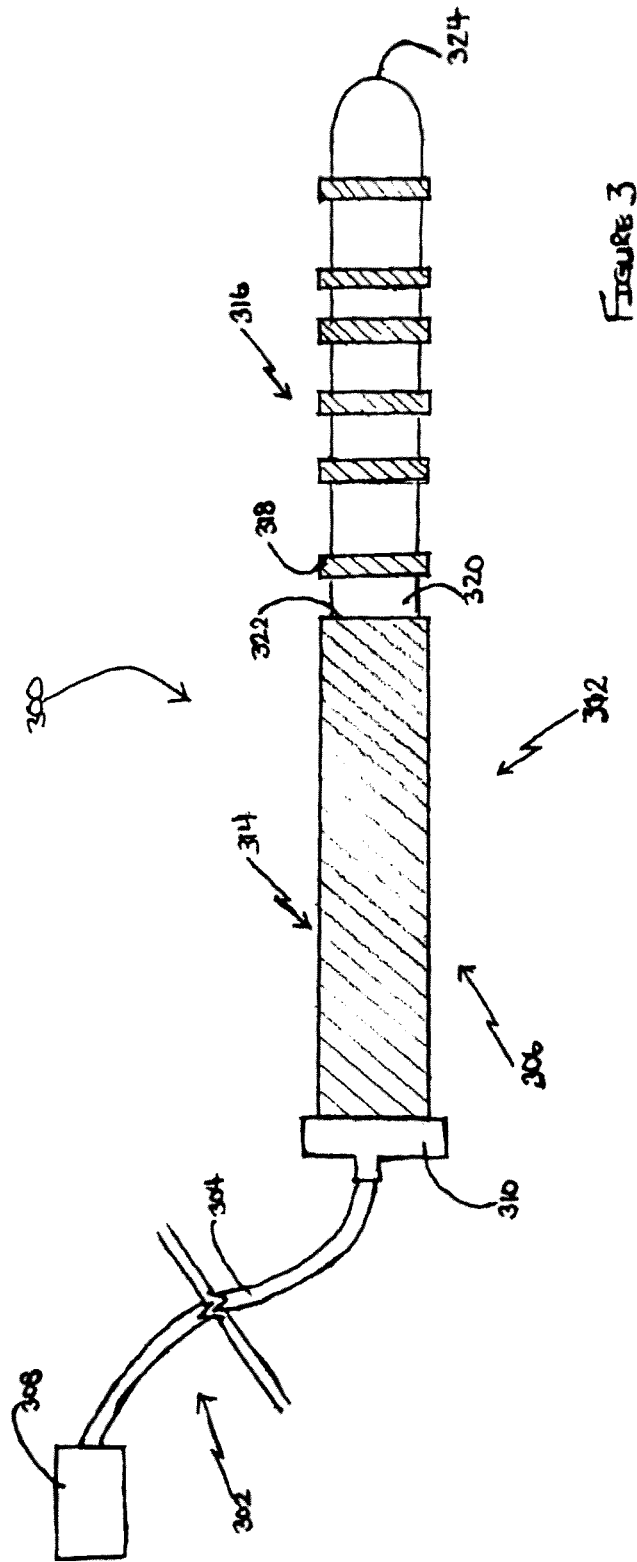
FIG. 3 is a side view illustration of one embodiment of an apparatus of the present invention.

Referring now to FIG. 3 and in accordance with one embodiment of this aspect of the present invention, an electrosurgical device 300 with discontinuous electrical conductivity is provided. From a proximal to a distal end, device 300 may comprise a proximal region 302, a probe cable 304 and a distal region 306. The term 'proximal' is used to refer to a portion or region of a device or tissue that is located closest to the user of the device, while 'distal' refers to a portion or region of a device or tissue that is located closest to a treatment site or furthest away from the user. Proximal region 302 may comprise an electrical connector 308 for connecting device 300 to an energy source (not shown). Probe cable 304 provides an electrical connection from electrical connector 308 to a hub 310 located in distal region 306. Distal region 306 further comprises an electrically conductive probe 312 with an insulated portion 314 and an active portion 316. The probe may be any elongate device comprising an active portion for delivering energy which may be percutaneously inserted into a patient's body. These devices include but are not limited to catheters, cannulae and electrosurgical probes. For the sake of clarity, the term probe is used throughout the specification to describe any such device. The active portion of the probe refers to the portion through which energy may be delivered to the surrounding environment. The active portion may include one or more electrical discontinuities and may, in some embodiments, for example as shown in FIG. 3, include the entire portion of the probe from the distal-most electrically exposed and conductive surface to the proximal-most electrically exposed and conductive surface. Active portion 316 may be one example of an energy delivery means for delivering energy to a target site within a patient's body. In some embodiments, probe 312 may be substantially rigid such that the relative positions of the regions of electrical discontinuity are not affected by the tissue being treated. For example, in one embodiment, a substantially rigid probe won't bend significantly if it is placed adjacent a tissue surface that is 'curvy' or 'bumpy'. In addition, any references to an 'insulator', 'insulating material' or 'insulated region', may refer to a material or region that is at least electrically insulated (unless otherwise stated), although it may be thermally insulated as well.

Probe 312 may be used to deliver energy to a patient's body and may be connected to cable 304 within hub 310. In accordance with this embodiment of the present invention, active portion 316 comprises at least one insulated region 318 and at least two electrically conductive and exposed regions 320, wherein the at least two conductive regions 320 are separated by the at least one insulated region 318. In such an embodiment, probe 312 may be said to have three regions of electrical discontinuity, as described above. In the illustrated embodiment, probe 312 has seven insulated regions 318 and eight conductive regions 320. The longitudinal length of the individual conductive regions may vary along the length of active portion 316 and may be least near the middle of active portion 316 and greatest nearest the two ends of active portion 316. For example, the lengths of the eight conductive regions, from a proximal end 322 to a distal end 324 of active portion 316, may be as follows: about 8 to about 12 mm, about 3 to about 5 mm, about 3 to about 5 mm, about 1 to about 3 mm, about 1 to about 3 mm, about 3 to about 5 mm, about 2 to about 4 mm and about 10 to about 14 mm. Insulated regions 318 may be about 2 to about 4 mm long and the length of active portion 316 may be about 50 to about 80 mm. In alternate embodiments, active portion may be at least 10 mm in length and, more specifically, at least 15 mm in length. It should be noted that the number of insulated and conductive regions, as well as the lengths of the conductive regions and insulated regions, may vary and the invention is not intended to be limited in this regard. In certain embodiments, the lengths of the individual conductive and insulated regions may be identical, while in other embodiments, including the embodiment shown in FIG. 3, the lengths may differ. In further embodiments, one or more properties of the insulated or conductive regions may be variable during a treatment procedure. For example, the position of insulated regions 318 or the lengths of insulated regions 318 may be variable during the course of a treatment procedure.

Insulated regions 318 may comprise thin bands of insulating material, described in more detail below, circumscribing probe 312. The insulating material may be, for example, about 0.02 to about 0.10 mm (about 0.001 to about 0.004 inches) thick and the thickness may vary depending on the specific material used. In alternate embodiments, the insulated regions may not completely circumscribe probe 312 but may only cover about 180° of the circumference. In yet further embodiments, the insulated regions may take on any shape and may circumscribe any portion of probe 312 and the invention is not limited in this regard.

Probe 312 may be straight or it may have one or more curves or bends anywhere along its length or may have a shape that is able to be changed, either manually or automatically. As used herein, 'curves or bends' refers to any deviation from a longitudinal axis of probe 312. Similarly, although the illustrated embodiment comprises a blunt distal end 324, distal end 324 may be sharp or may take on any other shape and the invention is not limited in this regard. In addition, probe 312 may be solid but, in alternate embodiments, it may be hollow and may contain one or more channels or lumens.

In the embodiment shown in FIG. 3, probe 312 may be about 160 to about 260 mm in length and, more specifically, about 180 to about 240 mm in length. Similarly, the gauge of probe 312 may be in the range of about 16 to about 24 AWG (about 0.6 to about 1.4 mm in diameter) and, more specifically, about 18 to about 22 AWG (about 0.7 to about 1.0 mm in diameter). However, the total length of the probe, as well as the gauge or diameter, may vary. Furthermore, although FIG. 3 shows a hub 310, the device may or may not have a hub depending on a user's preference and the specific intended application of the device. In the embodiment shown in FIG. 3, probe cable 304 may be about 30 to about 90 cm in length and, more specifically, about 45 to about 75 cm in length but this length may vary depending on a user's requirements. Furthermore, in some embodiments no cable may be required and the probe may communicate with an energy source through other means, such as wireless communication. Alternatively, the device 300 may be internally-powered, for example by using a battery. Electrical connector 308 may be any connecting means operable to provide an electrical connection between cable 304 and an energy source. In one embodiment, connector 308 comprises a 4-pin medical connector capable of being automatically identified when connected to the energy source.

Material

According to one embodiment of the present invention, probe 312 may be fabricated from stainless steel. However, any biocompatible and electrically conductive material, including but not limited to nickel-titanium alloys, may be used, depending on the desired structural properties of the probe. For example, in applications requiring a stiffer and stronger probe, stainless steel may be desirable, while a nickel-titanium alloy may be used for applications requiring superior flexibility and/or shape memory. The insulating material used to insulate probe 312 along insulated portion 314 as well as along insulated regions 318 may be polytetrafluoroethylene (PTFE) but any insulating material, including but not limited to polyethylene terephthalate (PET), may be used. For example, in alternate embodiments, the insulating material may be semi-porous to allow for some leakage of current through the insulating material. It should be noted that different insulating materials can be used for different portions of probe 312. For example, the insulating material used to insulate probe 312 along insulated portion 314 may or may not be the material used to insulate probe 312 along insulated regions 318.

Method of Manufacture

In one method of manufacturing the embodiment as described above, insulating material is applied overtop of an electrically conductive probe and is selectively removed in order to define insulated regions 318 and conductive regions 320. Alternatively, at least one pre-formed band of insulating material may be applied by being placed overtop of the probe and then adhered to the probe, for example by using a glue, epoxy or other adhesive, or by applying energy to shrink the insulating material to the probe. In such embodiments, active portion 316 may comprise a single electrode for delivering monopolar energy to a target site. Such an embodiment may be useful, for example, in applications where it would be desirable to provide substantially monopolar and/or monophasic energy along active portion 316. In an additional method of manufacturing a device of the present invention, the probe, rather than being constructed from conductive material and subsequently overlain with insulating material, is initially constructed from both conductive and non-conductive material fused or otherwise joined together to form a probe with a desired placement of conductive and non-conductive regions. In another embodiment, separate insulated and conductive regions may be formed by the treatment of a material in order to alter its electrical properties. For example, a conductive probe could be overlain by a material that allows electrical current to pass freely through it, but which, when subjected to a certain treatment, becomes insulating in nature. The treatment of selected sections of the probe in this manner could be used to disrupt the conductivity of the probe. Alternatively, the probe itself could be treated in some way to render portions of the probe non-conductive. Furthermore, a probe may be manufactured from an insulating material that could then be treated or overlain in a process that renders portions of the probe conductive. In such an embodiment, active portion 316 may comprise two or more discrete electrodes, each of which may be operable to deliver electrical current at the same or at different electrical poles and/or phases. For example, such a probe may be operable in a bipolar or triphasic configuration.

Alternate Embodiments

Figure 4:
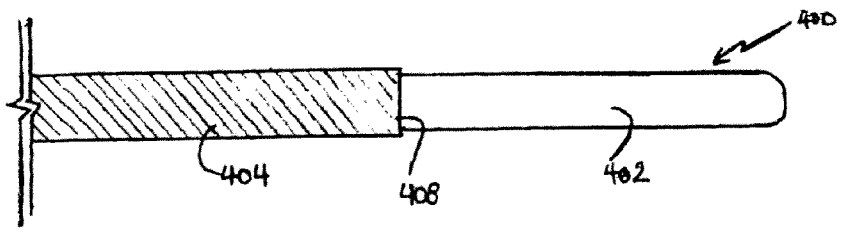
FIGS. 4-6 are side view illustrations of alternate embodiments of a probe of the present invention.

In an alternate embodiment of a device of the present invention, an electrical discontinuity may be achieved by adjusting the relative positions of insulating and conductive regions of the device. For example, as shown in FIG. 4, an apparatus of the present invention may comprise a probe 400 slidably disposed within an introducer 404. The term 'introducer' is not limited to a specific device but rather describes any device that may accomplish the same function as the introducer described herein. In use, probe 400 may be inserted into a region of tissue through a lumen of introducer 404, with an active portion 402 of probe 400 extending longitudinally beyond a distal end 408 of introducer 404. Introducer 404 may be insulated such that distal end 408 of introducer 404 may serve as an insulated region/conductive region boundary, or electrical discontinuity as has been described above. The insulated introducer may be one example of an insulating member or a means for electrically insulating the apparatus. During the course of treatment, a position of this electrical discontinuity may be altered by, for example, retracting or advancing distal end 408 of introducer 404, thus changing the effective length of active portion 402. Alternatively, the boundary position may be adjusted by retracting or advancing probe 400 into the tissue. By adjusting the position of introducer 404 with respect to probe 400, the boundary between the insulating and conductive regions of the apparatus, which corresponds to an electrical discontinuity, or area of relatively high current density, is moved with respect to the tissue. Thus, the position of the boundary may be adjusted, for example during energy delivery, in order to achieve an optimal current density profile for creating a lesion of a specified size and shape, for example a substantially homogeneous lesion, which, in this embodiment, may or may not also be a strip lesion. A strip lesion, as used herein, may refer to a lesion which is elongate, i.e. its length substantially exceeds at least one of its other two dimensions. A strip lesion may be substantially straight or curved. In other embodiments incorporating a sheath or introducer device, the sheath itself may not be fully insulated but may be discontinuously conductive, in accordance with embodiments of the present invention. As stated above with respect to the 'introducer', any references to a 'sheath' is not limited to a specific device but rather describes any device that may accomplish the some function as the sheath described herein.

Figure 5:
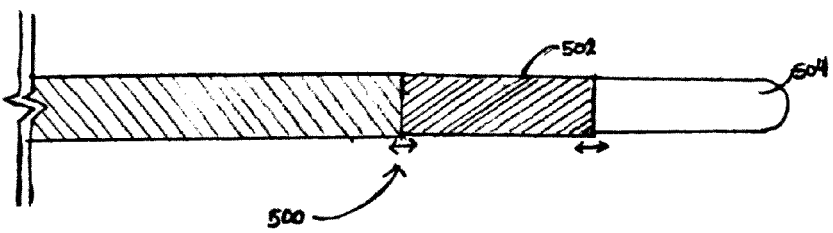

In a further embodiment of a device of the present invention, the device comprises a telescopic probe having at least two telescoping segments that are independently retractable and/or extendable or which may be advanced with respect to one another. An exemplary device of such an embodiment is illustrated in FIG. 5. FIG. 5 shows a probe 500 having an insulating sleeve or insulating member 502 and an active portion 504, wherein the positions of insulating member 502 and active portion 504 may be independently adjustable, thus allowing the position of an electrical discontinuity at the insulated region/conductive region boundary to be altered before, during or after the course of a treatment procedure. For example, as mentioned above, the position of the electrical discontinuity may be adjusted during a step of delivering energy in order to create a substantially homogeneous lesion.

Figure 6:
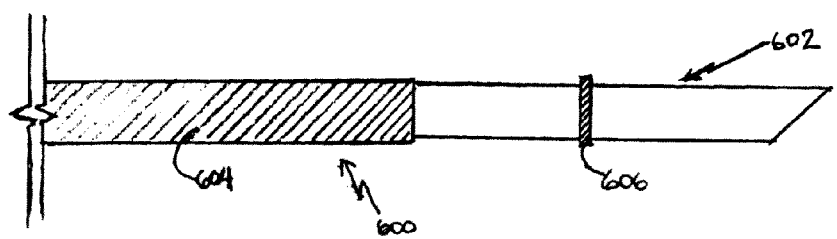

Referring now to FIG. 6, an additional embodiment of a device of the present invention is shown. In this embodiment, probe 600 comprises a cannula 602 adapted to be insertable into and through an introducer device 604. Cannula 602 may be manufactured from a conductive material and comprises at least one insulated region 606 disposed at some position along an active portion of cannula 602. The term 'cannula' is not limited to a specific device but rather describes any device that may accomplish the same function as the cannula described herein. Insulated region 606 provides an electrical discontinuity along cannula 602 and, as has been described earlier, it is theorized that this discontinuity may allow for a substantially homogeneous distribution of current density radiating from cannula 602. This specific embodiment of a device of the present invention may be useful in extending the usable lengths of the active portions of electrosurgical cannulae. For example, due to the fact that current density may be concentrated around an electrical discontinuity, it may be difficult to create a lesion along the entire active portion of a cannula having a relatively long active portion, because the current may be concentrated around the electrical discontinuities present at the insulating region/conductive region boundary of the cannula, as well as at the cannula tip. However using a device of this embodiment of the present invention, a substantially homogeneous lesion may be created along a greater portion of the length of the active portion of the cannula due to the inclusion of an insulating band 606 along the active portion of the cannula. As described above, insulating band 606 may help to create a more effective distribution of current density due to the 'edge effect' and 'hot spot' phenomena. Once again, it should be noted that, although a specific theory of operation has been described, the various embodiments described in conjunction with the present invention are not intended to be limited to this or any other theory of operation.

Figure 7:
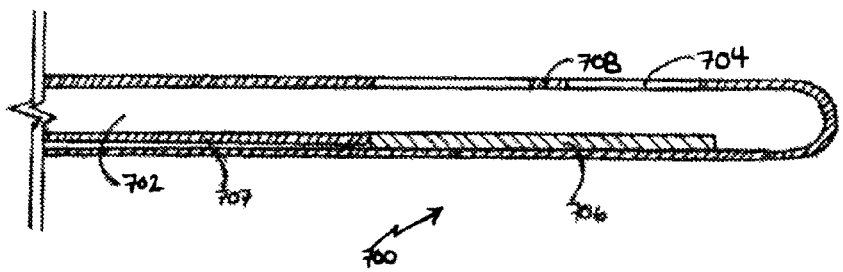
FIG. 7 is a longitudinal cross section through the middle of an alternate embodiment of a probe of the present invention.

In an alternate embodiment of a device of the present invention, shown in cross-section in FIG. 7, a probe 700 defines a lumen 702 in fluid communication with at least one aperture 704 located at a distal portion of probe 700. Aperture 704, shown on a lateral portion of probe 700 may be located anywhere along the distal portion of probe 700, including at a distal tip or distal end of probe 700. Probe 700 may further comprise an electrode 706 for energizing a conductive fluid that may be introduced through lumen 702. Electrode 706 may be connected to an energy source (not shown) via a wire 707 or via other means for electrically connecting an energy delivery device. In addition, probe 700 comprises a flow impeder 708 for interrupting the flow of a fluid through aperture 704. Flow impeder 708 may function similarly to the insulating bands described in conjunction with the aforementioned embodiments of the present invention. In other words, flow impeder 708 may serve to create a more homogenous flow of fluid through aperture 704 by creating additional boundaries to fluid flow, resulting in 'hot spots' or regions of increased fluid flow density around flow impeder 708.

Additional embodiments of a device of the present invention may include various electrosurgical devices that deliver energy or another treatment composition during the course of a treatment procedure. Examples of such devices include but are not limited to electrosurgical knives or blades and radiofrequency ablation catheters and probes. Such devices may benefit from the inclusion of some type of flow impeder or means for impeding flow, as has been described in accordance with the present invention. A flow impeder may comprise a region of insulating material, which impedes the flow of current along the length of a probe. Alternatively, a flow impeder may comprise a fluid flow disrupter, as in the embodiment described in FIG. 7.

Features

In some or all of the aforementioned embodiments, as well as any other embodiments not specifically described herein, any or all of the conductive regions of the probe may be at the same electric potential and thus arranged to deliver energy in a monopolar configuration whereby energy may be transmitted from the probe to a separate reference electrode. In such embodiments, at least one of the conductive regions may be adapted to be connected to an energy source and the conductive regions may be electrically connected to each other. In other embodiments, one or more electrically isolated conductive regions, or groups of conductive regions, may lie at one or more different electric potentials as in a bipolar, triphasic, or other configuration. In this case, current will flow between the various conductive regions, or groups of conductive regions, primarily along the length of the probe, obviating the need for a separate reference electrode.

Additionally, in some or all of the embodiments of the present invention, the device may comprise one or more of: means for cooling the tissue adjacent a region of the probe (for example, by the circulation of a cooling fluid through an internal lumen of the probe), means for applying a force to change the shape of at least a portion of the probe (for example, using a spring or a guide wire or other means of actuation), means for facilitating the insertion of the probe into a patient's body (for example, an introducer, cannula and/or stylet), means for visualizing the probe once it has been inserted (for example, using a radiopaque marker in conjunction with fluoroscopic imaging or using some other imaging modalities including but not limited to CT, MRI and ultrasound), and one or more additional functional elements for performing a function on the tissue (such as adding or removing material). As has been mentioned, the probe may be substantially rigid or may have various degrees of flexibility. Furthermore, one or more regions or segments of the probe may be manually or automatically deformable or steerable.

Some embodiments of the device of the present invention may further comprise a means for measuring one or more tissue properties, including but not limited to temperature and impedance. The device may further comprise means for measuring pressure or other physical properties. The means for measuring temperature may comprise at least one thermocouple, thermistor, thermometer or other temperature sensor located anywhere along the length of the probe. In some specific embodiments, the probe may comprise a plurality of temperature sensors, for example one sensor per electrical discontinuity. The means for measuring pressure may comprise a lumen in fluid communication with fluid in a patient's body as well as with a pressure transducer to record the pressure measurements. In other embodiments, the pressure sensor may comprise a pressure transducer disposed at a desired location on the probe.

A means for measuring one of the properties mentioned above may optionally be used in conjunction with a means for controlling the operation of the device based on said measured properties. For example, in one embodiment, a device of the present invention is connected to an energy source configured to supply radiofrequency energy to the device. The device may comprise at least one temperature sensor connected to the energy source, whereby the supply of energy to the device can be controlled based on the measurements received from the at least one temperature sensor. For example, if the measured temperature exceeds a specified upper threshold, the energy source may perform a specified action, including but not limited to shutting down automatically or decreasing the power delivered to the device. In an alternate embodiment, the device comprises impedance sensors which are connected to the energy source and whereby the supply of energy may be controlled based on the measurements received from the impedance sensors. In additional embodiments, the operation of the device may be modified (based on measurements received from one or more sensors) in other ways, including but are not limited to, terminating the procedure, modifying the supply of a cooling means to the device, or affecting a change in the conductivity or impedance of the probe (for example, by altering the relative position of one or more electrical discontinuities, as described above). The operation of the device or the energy source may also be able to be manually controlled by a user, or may be automatically controlled based on other parameters, for example, based on a measurement of a property of the device itself, rather than a property of the tissue.

System

Figure 8:
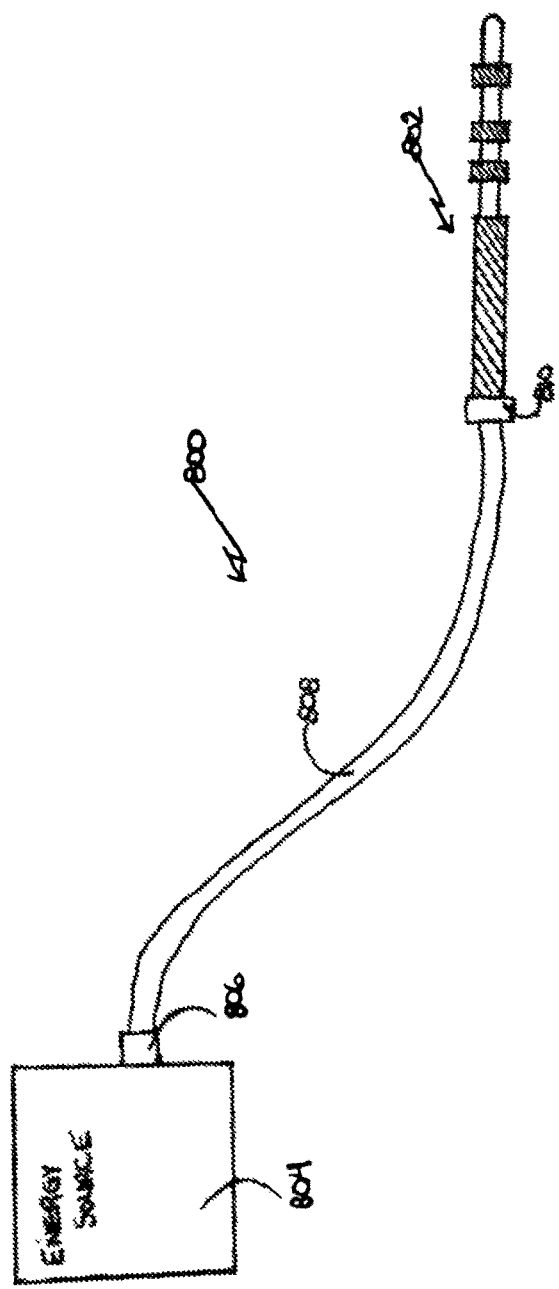
FIG. 8 shows an embodiment of a system of the present invention.

With reference now to FIG. 8, one embodiment of a system 800, incorporating a probe 802, is shown. System 800 preferably comprises an energy source 804, a proximal electrical connector 806, a probe cable 808, a distal electrical connector 810 and a probe 802.

Energy source 804 may be operable to deliver energy in the form of electrical current, for example in the radio-frequency (RF) range. In some embodiments, energy source 804 may be releasably coupled to probe 802. For example, this may be achieved by providing proximal and distal electrical connectors 806 and 810, at least one of which is releasable. In alternate embodiments, probe 802 may be permanently attached to energy source 804. Additionally, some embodiments may include other means of transmitting energy from energy source 804 to probe 802. In embodiments in which the device is cooled (as described above), probe 802 may further comprise releasable connectors (not shown), such as Luer locks, to couple one or more cooling means, such as peristaltic pumps and associated tubing, to probe 802. In alternate embodiments, probe 802 may be permanently attached to the one or more cooling means.

Method

One general application of a device of the present invention is for ablation of a target site at a region of tissue in a patient's body. If a sufficient amount of energy is delivered to a region of tissue using a device of the present invention, at a sufficient voltage to increase the heat of the tissue to or past the ablation temperature of the tissue, ablation will occur and one or more lesions will form in the vicinity of the device. As used herein, 'ablate', 'ablating' or 'ablation' may be understood as raising the temperature of a tissue such that at least a portion of the tissue is coagulated and a lesion is formed within the tissue. This ablation can include, but is not limited to ablation of one or more of: neural tissue, whose ablation can prevent the transmission of nociceptive sensation, structural or connective tissue, whose ablation can cause a contraction of collagen and a reduction in the volume of tissue, and vascular tissue, whose ablation may result in the disruption of nutrient supply to one or more neural structures. The specific geometry of the device and the relative positions of any insulated and conductive regions can affect the shape and size of any resulting lesions, as the density of current radiating from the device will be increased at the regions of electrical discontinuity, as has been described.

SI Joint

Figure 9:
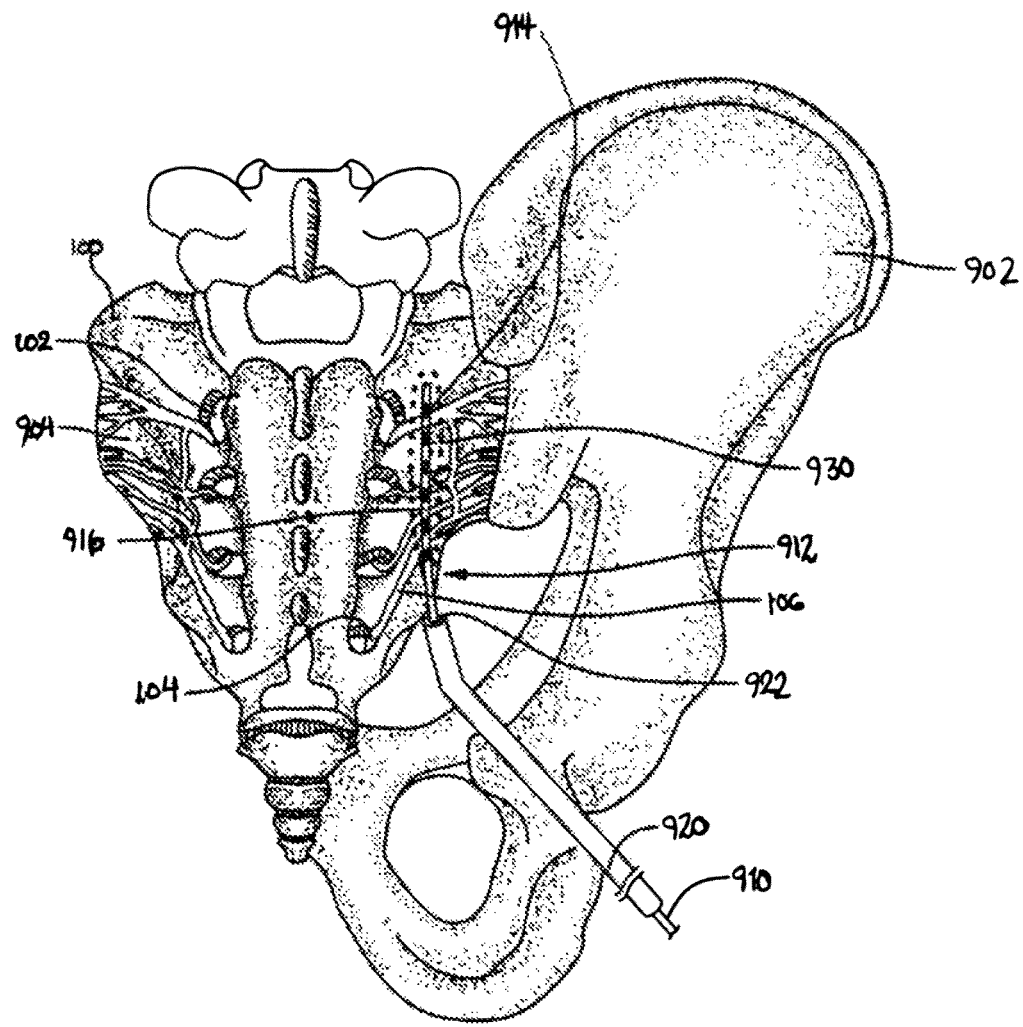
FIG. 9 is an illustration of a sacroiliac region of a patient's body, showing one application of a method embodiment of the present is invention.

One specific application of a device of the present invention is for the treatment of sacroiliac syndrome. Pain or other symptoms (described below) associated with or emanating from the sacroiliac region have been referred to in the literature as sacroiliac syndrome, sacroiliac joint dysfunction or sacroiliac joint complex (SIJC) pain, amongst other terms, and, for clarity, will be referred to throughout this specification as 'sacroiliac joint syndrome' (SIJS). Symptoms of sacroiliac joint syndrome may include, but are not limited to: pain, stiffness and tingling. Referring to FIG. 9, the SI joint 904 is the joint between the sacrum 100, a large bone at the base of the spine composed of five fused vertebrae, and the ilium 902 of the pelvis. SI joint 904 is a relatively immobile joint, serving to absorb shock during locomotion. The structure of the SI joint varies significantly between individuals but generally comprises an articular cartilaginous surface, a ligamentous aspect and, in most cases, one or more synovial recesses. Though the specific pathways of innervation of the SI joint have not yet been elucidated, the nerves responsible for sacroiliac joint pain are thought to comprise, at least in part, nerves emanating from the dorsal sacral plexus, the network of nerves on the posterior surface of the sacrum, extending from the sacral nerves 104, also referred to as the posterior primary rami 104, that exit the sacral foramina (posterior sacral foramina) 102. Diagnostic criteria for SIJS include the following: (1) pain in the region of the SI joint with possible radiation to the groin, medial buttocks, and posterior thigh, (2) reproduction of pain by physical examination techniques that stress the joint, (3) elimination of pain with intra-articular injection of local anesthetic and (4) an ostensibly morphologically normal joint without demonstrable pathognomonic radiographic abnormalities. While mechanical support devices exist for the alleviation of pain, there is currently no standardized method or apparatus for the treatment of SIJS.

With respect to the present invention, one embodiment of a method of treating the sacroiliac region of a patient's body by delivering energy may generally comprise the following steps: inserting a treatment device, for example a probe, into a target site within the sacroiliac region of a patient's body; and delivering energy to the treatment device to treat tissue within the target site. The treatment device may be a probe as described herein above, for example a substantially rigid probe that may be able to create a strip lesion during a single energy delivery step. In addition, the probe may have at least two regions of electrical discontinuity as described above. Two broad aspects of a method embodiment of treating the sacroiliac region by delivering energy will be presently described.

First Aspect

In accordance with a first aspect of a method embodiment of the present invention, a method for the treatment of SIJS by performing a treatment procedure outside of the SI joint is provided. The method generally comprises the steps of inserting a device, for example a probe, into a region of tissue external to the SI joint in a patient's body and performing a treatment operation in order to reduce one or more symptoms associated with SIJS. For example, a treatment procedure of this method aspect may be performed proximate to a patient's sacral region, within one or more of the SI ligaments or in a region of tissue adjacent to one or more nerves that innervate the SI joint. These locations are exemplary only and are not intended to limit the present invention in any way. The scope of this aspect of a method embodiment of the present invention is intended to cover any treatment procedures performed external to the SI joint that fall within the limitations of the appended claims. This approach is beneficial because it may allow for a treatment procedure that can effectively target neural tissue that innervates the SI joint without having to actually enter the joint itself. Furthermore, if a patient's pain is emanating from the SI joint ligaments, it may be beneficial to target the neural tissue before it reaches the ligaments in order to alleviate this pain. In addition, energy may be delivered to connective tissue in the SI region (such as, for example, one of the sacroiliac ligaments) in order to, for example, tighten or loosen the tissue. Generally, it may be beneficial to treat neural tissue as close to the nerve root as possible, in order to increase the effectiveness of the treatment procedure.

A first embodiment of the first aspect generally comprises the steps of inserting one or more probes into a region of tissue in a patient's body and delivering energy through the probe(s) in order to relieve symptoms of SIJS, wherein the energy may be delivered, for example, in order to ablate tissue. Lesioning by ablation can for example be effected using an RF signal having a voltage up to about 500V, current up to about 5 amperes, a frequency of about 200 kHz to about 10 MHz and an application interval of about 5 seconds to about 30 minutes; for tissue in the sacroiliac region, the signal may, in some embodiments, have a voltage ranging between about 10V and about 200V, a frequency of about 400 to about 550 kHz, an application interval of about 1 to about 10 minutes, and a power of about 1 to about 20 Watts. In the embodiment shown in FIG. 9, a probe 910, comprising an active portion 912 and a proximal region (not shown), is inserted proximate to sacrum 100. In this embodiment, probe 910 comprises insulated regions 914 and conductive regions 916 associated with active portion 912, and probe 910 may be operable in a monopolar configuration in conjunction with a grounding pad (not shown) placed at some location on the surface of the patient's body. Probe 910 may be able to create a lesion 930, for example a strip lesion 930, adjacent sacrum 100, in order to treat as many neural structures of the dorsal sacral plexus as possible within a single treatment procedure. However, the ability to create a strip lesion is not necessary in some embodiments. Rather, various probes, capable of producing lesions of various shapes and sizes, may also be used in conjunction with this aspect of the present invention and the invention is not limited in this regard.

Referring now to the steps in detail, the step of inserting a device into a region of tissue may comprise penetrating into the tissue using one or more rigid introducer tubes or other insertional apparatus, and inserting the probe(s) through the introducer(s). Penetration into the tissue may also be facilitated by the use of a sharp or pointed probe(s), by the use of a stylet, by the insertion of a guide wire or by any other insertional method or device and the invention is not limited in this regard. It should also be noted that the introducer(s) or other means for insertion may or may not be electrically and/or thermally insulated and they may be curved or straight. Furthermore, the length and diameter of the introducer are not limited to specific values and any suitably sized introducer may be used. As noted above, the term introducer is used throughout this specification and is intended to encompass any device that may facilitate entry of the probe into a specific site within the body of a patient. In such embodiments, these devices may be capable of penetrating into a patient's body as well as penetrating through one or more of the ligaments of the sacroiliac region. In alternate embodiments, the probe may be positioned at the appropriate location within a patient's body without using any additional means to facilitate insertion.

In some embodiments of the present invention, a supporting or stabilizing apparatus or device may be used to help prevent inadvertent movement of the probe(s) and/or introducer(s). For example, the supporting or stabilizing apparatus (i.e. a means for supporting or stabilizing) may, for example, take the form of a frame for fixing the probe(s) and/or introducer(s) in a desired position. During the step of inserting the probe(s), the position of the probe(s) or introducer(s) may be visualized and/or monitored, for example by using fluoroscopy or other imaging modalities. If fluoroscopy is used, visualization may be improved by incorporating one or more radio-opaque markers onto one or more of the probe(s) or introducer(s). In some embodiments, radio-opaque markers may be incorporated onto a distal region of the probe(s) in order to determine the distance that the probes are extending out of the introducer(s). In addition, visual depth markers may be used to help determine the position of the probe(s) or introducer(s) within the body. Furthermore, positioning may be confirmed by measuring the impedance of tissue at the location of the probe(s) or introducer(s), as is known in the art. In some embodiments, positioning may not be verified using these means and a user may rely in whole or in part on his knowledge of a patient's anatomy in order to accurately place the device(s).

Referring now to the step of delivering energy through the probe(s), this may be accomplished for example by providing a generator, operable to deliver radiofrequency (RF) energy, connecting the generator to the probe(s) and operating the generator to deliver said RF energy to the tissue through the energy delivery device associated with, for example, a distal region of the probe(s). Some details regarding an exemplary generator are recited below, with respect to a second aspect of the method of the present invention. In certain embodiments, the generator is operable to deliver sufficient energy to the tissue through the probe(s) so that the tissue may be ablated, as has been defined earlier. In such embodiments that involve the ablation of a region of tissue, the tissue ablated according to this method aspect of the invention can include, but is not limited to, neural tissue, whose ablation can prevent the transmission of pain sensation and vascular tissue, whose ablation may result in the disruption of nutrient supply to one or more neural structures. Furthermore, as described above, some embodiments of a method of the present invention may comprise delivering energy in a substantially homogeneous manner, in order to create a substantially homogeneous lesion. In alternate embodiments, the energy delivered by the generator through the probe(s) may not ablate tissue but may perform one or more other treatment functions such as altering the structure of collagen (without causing cellular coagulation). Alternatively, RF current, microwave current, or other energy could be delivered in a series of amplitude or frequency modulated pulses, whereby tissue heating is inhibited by interrupting periods of energy delivery with relatively long periods in which no energy is delivered. By pulsing the energy in this manner, a voltage that is sufficiently high to affect a prolonged disruption of the function of neural tissue may be used, while maintaining the tissue at a temperature such that no lesion will form, or such that the formation of a lesion will be inhibited. In further embodiments, a generator may not be used. In these embodiments, energy may be generated by a battery (in which case the entire system [probe and energy source] may be hand-held/portable/modular) or any other means and the invention is not limited in this regard. Any delivery of energy that may result in a treatment effect to alleviate one or more symptoms of SIJS is intended to be included within the scope of this aspect of the present invention.

Regarding connecting the generator to the probe(s), the generator may, in some embodiments, be releasably coupled to the probe(s). For example, this may be achieved by providing releasable electrical connectors at or proximate to the proximal region of the probe(s). In embodiments in which the probe(s) are cooled, the proximal region of the probe(s) may further comprise releasable connectors, such as Luer locks, to couple one or more means for cooling, such as peristaltic pumps and associated tubing, to the probe(s). In alternate embodiments, the probe(s) may be permanently attached to the generator and/or the one or more means for cooling.

In some embodiments, the probe(s) used in this method aspect of the present invention may be operable to treat a plurality of neural structures without the need for one or more of removal of the probe(s), reinsertion of the probe(s) or repositioning of the probe(s). For example, at least two branches of the sacral nerves 104 may be treated. These two branches may comprise, for example, two or more branches of the same sacral nerve. Treatment of two or more branches of the same sacral nerve may be facilitated by delivering energy to at least a portion of a sacral neural crescent, as described above and as shown in FIG. 1. In such an embodiment, the method may comprise the step of delivering energy to a sacral neural crescent to create a substantially homogeneous lesion to treat at least two branches of a sacral nerve passing through the sacral neural crescent. Alternatively, these two branches may comprise at least one lateral branch 106 from one sacral nerve and at least one lateral branch 106 from a different sacral nerve.

One way of achieving this effect is to create a single strip lesion at a desired location, wherein said single strip lesion may be of sufficient size so as to affect multiple neural structures. As has been mentioned, the probe(s) may be operable to create such a lesion during the course of a single energy delivery step or while the probe remains in a substantially static position, i.e. without the need for one or more of removal of the probe(s), reinsertion of the probe(s) or repositioning of the probe(s). Thus, as used herein, a 'single energy delivery step' may refer to a single temporally continuous period of energy delivery. For example, creating a strip lesion in a single energy delivery step may allow for movement of one or more portions of the probe to create the strip lesion, as long as the delivery of energy is maintained during any such probe movement. In some embodiments, as discussed earlier with respect to the device aspect of the present invention, the relative positions of one or more portions of the probe may be adjusted during the energy delivery step. For example, the probe may comprise an active portion slidably disposed within an insulating member, wherein the relative positions of the active portion and insulating member may be adjusted by, for example, advancing or retracting one or more of the insulating member and the active portion. Adjusting the relative position of the active portion and insulating member results in a repositioning of the electrical discontinuity present at the boundary therebetween, which in turn may facilitate the creation of a substantially homogeneous lesion, for example a strip lesion. Alternatively, the probe may remain in a substantially static position during the creation of the strip lesion. It should be noted, however, that creating strip lesions through one or more probe repositioning steps, as well as creating individual, non-strip lesions, on one or more neural structures or other bodily material, also falls within the scope of this aspect of the present invention.

In addition, this aspect of the present invention is not limited to using only one probe and several probes may be used with this treatment method. Furthermore, each of these probes may comprise one or more conductive regions and the invention is not limited in this regard. For example, in alternate embodiments, two or more probes may be used in a bipolar configuration. In such embodiments, the probes may, for example, be spaced apart by a distance that is not greater than five times the diameter of the energy delivery device located on the probes. In other embodiments, probe separation may vary and may be more or less than the aforementioned maximum and minimum distances. In yet further embodiments, three or more probes may be used in a triphasic configuration.

As a feature of this aspect of the present invention, some embodiments may further comprise a step of moving the probe(s) to another location within the tissue if the user so desires. The probe(s) may be moved before, during, or after the step of delivering energy, and may be moved one or more times. The step of moving the probes may comprise one or more of the following actions: applying a force to bend the probe within the tissue (wherein the probe may thus be described as a 'steerable' probe), moving the probe intact within the tissue, removing the probe intact from the tissue, reinserting the probe into the tissue and moving one or more parts of the probe (for example, extending or retracting a segmented probe telescopically) to move the position of one or more functional elements within the tissue. For example, one such embodiment of this method aspect may comprise a step of repositioning a probe at another sacral neural crescent, wherein energy may be delivered to treat tissue within the other sacral neural crescent.

Thus, in one embodiment of this aspect of the present invention, and with reference again to FIG. 9, a method for treating SIJS may be practiced as follows: a patient is made to lie prone on an operating table or similar structure, a grounding pad is placed on the surface of the patient's body and local anesthetic is provided. Prior to the insertion of the probe(s) or introducer(s), fluoroscopic imaging or other means may be used to visualize a patient's sacroiliac region in order to ascertain the desired approach for inserting the device(s) into the desired tissue. This is particularly important with respect to SIJS treatment procedures because the anatomical structures involved may vary significantly from patient to patient. In one embodiment, a probe 910, operating in a monopolar configuration, would be positioned in proximity to the posterior sacral foramina 102, such that the step of delivering energy will result in an alteration of the function of the neural tissue of the dorsal sacral plexus. Therefore, in this embodiment, an introducer 920 may be inserted into a patient's body from a generally inferior-posterior approach under fluoroscopic guidance, such that a distal end 922 of introducer 920 is positioned proximate to or adjacent the inferior margin of sacrum 100. For example, in some embodiments, a substantially cranial-caudal or caudal-cranial approach may be utilized, wherein introducer 920 and/or probe 910 are inserted substantially along the cranial-caudal/inferior-superior axis of the patient's body, which allows for a relatively straightforward insertion procedure. It should be noted that, in the context of these embodiments, an approach substantially along the cranial-caudal axis is not intended to refer to an insertion along precisely this axis of the patient's body. Rather, there may be some lateral/medial and/or anterior/posterior components to the approach vector as long as the approach to the sacrum is not impeded by anatomical obstacles, such as the iliac crest, that may have to be negotiated. In other words, this approach is intended to allow for a fairly straightforward insertion into the target site. In alternate embodiments, other approaches, such as, for example, a more lateral approach may be used, depending on the user's preference.

In some embodiments, distal end 922 of introducer 920 is positioned immediately adjacent to the bone, without any ligaments or other connective tissue in between distal end 922 and sacrum 100. In other embodiments, various angles of approach and sites of entry may be used. Depending on the site of entry and the angle of approach that are chosen, the introducer may be either curved or straight. A curved introducer may take several forms and the invention is not limited in this regard. For example, it may be curved along a substantial portion of its radius or it may have a bent tip, wherein the rest of the introducer may be straight. In addition, the active portion 912 of probe 910 may be curved or straight.

At this point, and with reference again to FIG. 9, the position of introducer 920 may be verified using fluoroscopic imaging (or other imaging modalities) or other means, after which probe 910 may be inserted through a bore or lumen of introducer 920 such that at least a portion of active portion 912 of probe 910 is located adjacent to and along sacrum 100. It should be noted that, in those embodiments that comprise a stylet to facilitate positioning of the probe, the stylet may be located within an introducer and may be removed from the introducer prior to insertion of the probe. As shown in FIG. 9, probe 910 may be advanced to the extent that lesion 930 will be created around probe 910 across a substantial part of the dorsal sacral plexus when energy is delivered to conductive regions 916. In this embodiment, it may be beneficial to use a flexible probe which is capable of conforming to the surface of sacrum 100. In other embodiments, the probe may extend various distances outside of the introducer and the invention is not limited in this regard. For example, if using a brush electrode comprising a plurality of electrically conductive filamentary members, an effective lesion may be created by dragging the probe along a tissue while supplying energy to the filaments, analogous to painting with a paint brush. In such an embodiment, the probe may be extended from the introducer such that a distal end of the probe may be located adjacent to the SI sacral nerve of the sacral posterior rami, so that, when the probe is retracted back into the introducer, a lesion will be created covering all of the nerves between the S1 level and the location of the introducer. In further embodiments, the probe(s) may be placed within a sacral neural crescent, as shown in FIG. 1, in order to treat lateral branches 106 of sacral nerves 104 as they exit sacral foramina 102.

It is advisable, at this stage, to ascertain the location of probe 910 with respect to any sensory and/or motor nerves that may be located nearby by stimulating the neural tissue at one or more physiological stimulation frequencies and determining the effect of said stimulation, as will be described in more detail below. Using this step, it can be determined whether a target nerve or group of nerves has a function that would contraindicate its ablation or functional alteration. In some embodiments, the lack of a contraindication would lead to the step of delivering energy, whereas the presence of a contraindication would lead back to the step of inserting a probe or probes, whereby the step of inserting a probe or probes comprises modifying the position of a probe or probes within the body. In alternate embodiments, no stimulation is performed and a user may rely on his or her knowledge (for example, of the patient's anatomy) to determine whether or not to proceed with the treatment procedure.

At this point, energy may be delivered from the generator (not shown) via conductive regions 916 to the region of tissue located proximate to conductive regions 916. If the probe is steerable, the probe tip may be maneuvered into a second location and energy may again be delivered to ablate the neural tissue at the second location. This may be repeated as many times as the user feels is necessary. If the probe is not steerable, the insertion and positioning steps may be repeated so that the probe is located at a second position, at which point energy may be delivered again at this location. For example, as mentioned above, the second location may be another sacral neural crescent, located on another level of the sacrum. Once the user has determined that enough neural tissue has been ablated or otherwise affected, the introducer and probe may be removed from the body and the patient should be allowed to recover. It should be noted that this description is intended to be exemplary only and that other embodiments are envisioned as well. In addition, this invention is not intended to be limited by the number and type of probes used in this and other embodiments as well as the number and type of lesions created by these probes.

Relief of SIJS symptoms may result from the fact that the neural tissue that may be affected by this procedure innervates the SI joint and thus, by treating the neural tissue external to the joint, pain transmission from the joint itself may be indirectly affected. As has been described, treatment of the neural tissue may be accomplished by the delivery of RF energy supplied to the probe(s) by a generator. Each probe may be furnished with one or more electrodes, and one or more probes may be used. If two or more electrodes are used, the electrodes may be in a monopolar, bipolar, multipolar, or multiphasic configuration. For example, several probes may be operated in a monopolar configuration, whereby a specific lesion shape may be obtained by determining an optimal spacing between probes that may produce a specific interference pattern and thus, a specific current density resulting in a desired lesion shape. Energy may be delivered to ablate at least a portion of the neural tissue of the dorsal sacral plexus, in order to reduce pain associated with the SI region. Alternatively, energy may be delivered in order to alter the function of the neural tissue of the dorsal sacral plexus, without damaging is the neural tissue, for example by delivering energy in a series of amplitude or frequency modulated pulses, as described above. Furthermore, as was mentioned above, energy may be delivered in order to perform some other treatment function that may result in relief of symptoms due to SIJS. For example, energy may be delivered to one or more of the sacroiliac ligaments in order to repair some defect in the ligaments or to tighten or loosen the ligaments. In addition, applying a treatment procedure (other than or in addition to neural ablation) external to the joint, for example, by heating one or more sacroiliac ligaments, may indirectly treat the joint itself as well (for example, by causing the shrinkage of collagen within the joint due to heat conduction from the ligaments).

In some embodiments, the steps of inserting one or more probes into a region of tissue in a patient's body and delivering energy through the probe(s), can be repeated one or more times, for example at each of the posterior sacral foramina as well as around the lower lumbar vertebrae. In other words, the steps described above may be used to alter the function of neural tissue around each of the posterior sacral foramina (for example, as described above with respect to treating tissue within the sacral neural crescents) as well as the lower lumber vertebrae. In other embodiments, the probe(s) may be inserted using an anterior approach, in which case the treatment procedure may involve the alteration of the function of neural tissue adjacent the anterior or posterior sacral foramina, for example within the anterior sacral neural crescents.

In alternate embodiments of this aspect of the present invention, energy may be delivered in forms other than radiofrequency electrical energy, including but not limited to: other forms of electromagnetic energy, for example microwave energy or optical energy; thermal energy; mechanical energy; and ultrasonic energy; and combinations thereof. Additionally, the step of delivering energy could involve the use of other energy delivery devices including, but not limited to: microwave probes, optical fibers, resistive heaters, and ultrasound emitters.

As was mentioned briefly above, the step of delivering energy to the tissue, may involve, in some embodiments, the use of devices in which the one or more probes are actively or passively cooled. Cooling of probes can prevent the searing or coagulation of tissue directly adjacent to the probe(s) and can prevent the vaporization of liquid within the tissue. Cooling can also be used to increase the maximum lesion volume that can be formed in a given tissue.

In addition to optionally measuring impedance, as in the embodiment described above, some embodiments further comprise an additional step of measuring the temperature of tissue at least at one location. This is generally desirable so as to ensure that a given region of tissue is not exceeding a certain temperature. For example, in some embodiments it may be desirable to maintain the temperature of tissue at or below a temperature required for neural ablation. Preferably, a means for monitoring temperature may be located on or within a distal region of the one or more probes and the temperature of tissue located proximate to the distal region(s) of the probe(s) may be monitored using the means for monitoring temperature. Alternatively or in addition, a means for monitoring temperature may be located at a different location on the one or more probe(s) to monitor the temperature of a region of tissue located some distance away from the distal region(s) of the probe(s). Furthermore, one or more separate means for monitoring temperature may be inserted into the patient's body in order to monitor the temperature of one or more specific regions of tissue. The means for monitoring temperature may take the form of one or more thermocouples, thermistors, optical thermal sensors or any other means for monitoring or sensing temperature and the invention is not limited in this regard. The means for monitoring temperature may be connected directly to the energy source (e.g. the RF generator) or they may be monitored by an independent temperature monitoring device. These embodiments are intended to be exemplary only and are not intended to limit the present invention in any way.

As a feature of this aspect of the present invention, the method may further comprise one or more steps of modifying a treatment procedure in response to one or more measured parameters. These measured parameters may include, but are not limited to, temperature, position of the probe(s) or impedance, or any combination thereof. For example, if a temperature measurement is determined to be outside of a desired range, a treatment procedure may be modified by, for example, altering the amount of energy delivered by the generator, modifying or modulating the one or more means for cooling in some way, or terminating the procedure. As another example, the amount of energy delivered by the generator may be modified based on the position of the one or more probes (for example, depending on the distance between a probe and the target treatment site or on the distance between the probes themselves when more than one probe is used). In such embodiments, a feedback system may be incorporated directly into the energy source so that any modification of a treatment procedure in response to a measured parameter may occur automatically. In other embodiments, there may not be an automatic feedback system in place, in which case a user may manually modify a treatment procedure in response to a measured parameter. In addition to modifying a treatment procedure based on measured parameters, this invention also provides for a step of determining the initial parameters to be used in a treatment procedure (for example, the initial maximum power level or tissue temperature, temperature ramp rate, etc.) using information that is known about the particular tissue to be treated. For example, if pre-treatment testing reveals specific information about the sacrum of a particular patient (this information may include, but is not limited to: the topology of the sacrum, location of specific nerves, etc.), that information may be used to decide on what parameters to use initially for the treatment procedure.

In some embodiments of this aspect of the present invention, the step of performing a treatment operation in order to reduce symptoms associated with SIJS may comprise the addition or removal of material to or from the body. Material that may be added to the region of tissue being treated includes, but is not limited to, alcohol, chemical lysing agents, pharmaceutical agents (including, but not limited to, anesthetics or other medicaments) or contrast media. Material that may be removed from the region of tissue being treated includes, but is not limited to, ligamentous tissue or other connective tissue. The removal of material may be accomplished through various means, which can include aspiration, vaporization or mechanical conveyance. Furthermore, the steps of addition and removal of material can be performed concurrently, for example by irrigating the tissue with a liquid medium while aspirating the liquid effluent. The addition or removal of material may also be combined with the delivery of energy, as has described above, wherein the delivery of energy and the addition or removal of material may occur concurrently or sequentially.

According to this aspect of the present invention, as has been described, one or more probes or other devices are placed at some location external to the SI joint. It should be understood that the probe(s) may be inserted into various locations and the invention is not limited in this regard. Furthermore, as has already been mentioned, a probe may be inserted using any approach that allows access to the desired tissue, including but not limited to: a superior posterior approach, an inferior posterior approach, or an anterior approach.

If more than one probe is used, the probes may be inserted into the tissue using different approaches. For example, when practicing this method aspect of the present invention using two probes in a bipolar configuration, as has been previously mentioned, the probes may be inserted at a relatively higher angle (i.e. closer to an anterior-posterior plane approach) with respect to the patient's body. When using probes in a bipolar configuration in this manner, it may be useful to follow a 'leapfrog' approach, wherein the two probes are inserted to initial locations and a lesion is created between the probes. Once the first lesion is created, the first probe is repositioned so as to be located on the other side of the second probe, for example more cephalad along the sacrum, and a second lesion is created. Following this, the second probe is repositioned so as to be located on the other side of the first probe, even more cephalad along the sacrum, and so on. This method can also be practiced by using a multiplicity of probes and leaving each probe in place. In other words, once a probe is in place it may remain there and further probes may be inserted in order to achieve this 'leapfrog' lesioning approach. In this way, an effective strip lesion may be created. In other embodiments, bipolar probes may be used in conjunction with various other approaches and this invention is not limited to using bipolar probes with this specific approach.

In embodiments of the present invention that employ more than one probe, the probes used during the course of a treatment procedure may form part of the circuit of an electrical impedance meter, as is known in the art, wherein energy may be transmitted between the probes through a region of tissue, allowing a user to determine the impedance of said region of tissue. This feature may be useful to determine whether or not the impedance of the tissue lies within a 'normal' range—if the impedance of the tissue is found to be outside that range, it may be indicative of an injury or defect within the tissue. As mentioned above, a single probe may also have an impedance measuring capability, for example to help determine the location of the probe within a patient's body.

Certain embodiments of the present invention may further comprise a step of performing a function to mop the neural pathways in the tissue and this step may occur one or more times throughout the course of the procedure. The step of performing a function to map the neural pathways in the tissue can involve, in some embodiments, stimulation of the neural tissue at one or more physiological stimulation frequencies and subsequent observation to determine the effect of said stimulation. Various frequencies and voltages can be used to stimulate both sensory and motor nerves, as is described herein below with respect to a second method aspect of the present invention. Observation of stimulation can take the form of visual, sensory, mechanical, or electrical detection of muscle activity, or the form of sensory or electrical detection of nociceptive or other sensory neural activity (e.g. temperature). Using this step, it can be determined whether a target nerve or nerves has a function that would contraindicate its ablation or functional alteration. In some embodiments, the lack of a contraindication would lead to the step of delivering energy, whereas the presence of a contraindication would lead back to the step of inserting a probe or probes, whereby the step of inserting a probe or probes includes modifying the position of a probe or probes within the body.

In an alternate embodiment of this first aspect of the method of the present invention, the method may comprise the steps of: positioning a treatment device, for example a probe, at a target site in proximity to an anatomical structure within the sacroiliac region; and delivering energy to the probe to treat the target site. In such an embodiment, the anatomical structure may impede the flow of electrical current such that a substantially homogeneous lesion may be created by the delivery of energy to the target site. For example, the anatomical structure may comprise bony tissue, for example on the surface of the sacrum, and the probe may be positioned in proximity to the sacrum such that the various crests and troughs of the sacrum act as means for impeding the flow of electrical current. In other words, the anatomical structure may function as an electrical discontinuity, which, as described above, may aid in the formation of a substantially homogeneous lesion.

Second Aspect

In accordance with a second aspect of an embodiment of a method of the present invention, a method for the treatment of SIJS by performing a treatment procedure within or adjacent to the SI joint is provided. Some embodiments of this aspect generally comprise the steps of: inserting a device into or adjacent an SI joint in a patient's body and performing a treatment operation in order to treat the SI joint and/or the surrounding region. For example, the method may comprise the steps of: positioning at least one probe, or a portion thereof, within or adjacent to a sacroiliac joint; and delivering energy through said at least one probe to create an intra-articular lesion, for example a substantially homogeneous lesion. Energy may be delivered in various configurations and may achieve various results, as will be presently described. This approach is beneficial because it may allow for a treatment procedure that can effectively target neural tissue that derives from both the anterior and posterior (also referred to as ventral and dorsal) primary rami. This approach also reduces the risk of inadvertently damaging crucial neural structures, such as motor nerves or large sensory nerve trunks, since it is designed to affect only the neural structures present within or adjacent the SI joint itself.

More specifically, a first embodiment of the method comprises the steps of: inserting at least one probe into or adjacent the SI joint and delivering energy through the probe(s), wherein the energy may be delivered in order to ablate tissue. In the embodiment shown in FIG. 10*a*, a probe 1040, comprising an active portion 1042 and a proximal region (not shown), is inserted into the intra-articular space (also referred to as the joint space) 1010 of the SI joint 904. In such an embodiment, probe 1040 may comprise insulated regions 1044 and conductive regions 1046 associated with active portion 1042, and probe 1040 may be operable in a monopolar configuration in conjunction with a grounding pad (not shown) placed at some location on the surface of the patients body. Preferably, probe 1040 is able to create a strip lesion 1050 within SI joint 904, in order to treat as much of the joint as possible within a single treatment procedure. Because the SI joint 904 is difficult to access, the ability to create a strip lesion to treat a large area with the insertion of only one probe is desirable in some situations. For example, a strip lesion having its longest dimension parallel to the longitudinal axis of the energy delivery device may have a length:width and/or depth ratio of approximately 3:1, i.e. the length substantially exceeds one or more of the width and/or the depth. Alternatively, another example of a strip lesion is a lesion that has its longest dimension on any axis other than an axis parallel to the longitudinal axis of the energy delivery device. Such a lesion may be created substantially between two or more probes, for example in a bipolar configuration. Alternatively, such a lesion may be created by a single probe. However, the ability to create a strip lesion is not necessary and, in alternate embodiments, the probe may indeed not be required to create or even capable of creating a strip lesion. Rather, various probes, capable of producing lesions of various shapes and sizes, may also be used in conjunction with this method aspect of the present invention.

Referring now to the steps in detail, the step of inserting at least one elongated probe may comprise penetrating into the joint using one or more rigid introducers 1030 or other insertional apparatus, and inserting the probe(s) through the introducer(s). Penetration into the joint may also be facilitated by the use of a sharp or pointed probe(s), by the use of a stylet, by the insertion of a guide wire or by any other insertional method or device and the invention is not limited in this regard. It should also be noted that the introducer(s) or other means for insertion may or may not be electrically and/or thermally insulated and they may be curved or straight. In the context of the present invention, the term 'curved' is taken to refer to a deviation from the longitudinal axis of the device. A curved introducer may take several forms and the invention is not limited in this regard. For example, it may be curved along a substantial portion of its radius or it may have a bent tip, wherein the rest of the introducer may be straight. Furthermore, the length and diameter of the introducer are not limited to specific values and any suitably sized introducer may be used. For clarity, the term introducer will be used throughout this specification and is intended to encompass any device that may facilitate entry of the probe into a specific site within the body of a patient. In embodiments that include such devices, these devices may be capable of penetrating into a patient's body as well as penetrating through one or more of the ligaments surrounding the SI joint. In alternate embodiments, the probe may be positioned at the appropriate location within a patient's body without using any additional means to facilitate insertion.

During the step of inserting the probe(s), the position of the probe(s) and/or introducer(s) may be visualized and/or monitored, for example by using fluoroscopy or other imaging modalities. If fluoroscopy is used, visualization may be improved by incorporating radio-opaque markers onto one or more of the probe(s) or introducer(s). In some embodiments, radio-opaque markers may be incorporated onto a distal region of the probe(s) in order to determine the distance that the probes are extending out of the introducer(s). In addition, visual depth markers may be used to help determine the position of the probe(s) or introducer(s) within the body. Furthermore, positioning may be confirmed by measuring the impedance of tissue at the location of the probe(s) or introducer(s), as is known in the art. In some embodiments, positioning may not be verified using these means and a user may rely in whole or in part on his or her knowledge of a patient's anatomy in order to accurately place the device(s).

More specifically, and with reference still to FIG. 10*a*, introducer 1030 may be inserted percutaneously about 1 to about 3 cm below the inferior margin 1014 of SI joint 904 and guided anterio-cranially until the tip 1032 contacts the ilium about 1 cm above inferior margin 1014. Introducer 1030 may then be manipulated until a tip of introducer 1030 enters the joint space. Probe 1040 may then be guided through introducer 1030 until a tip of probe 1040 enters intra-articular space 1010. Probe 1040 may then be further advanced to traverse intra-articular space 1010 of SI joint 904. Once probe 1040 is properly positioned, energy may be applied to create a lesion 1050 within SI joint 904. In an alternative embodiment and with reference now to FIG. 10*b*, introducer 1030 may be initially manipulated so that the introducer tip 1032 is placed just superior to the most posterior point of inferior margin 1014. Probe 1040 may then be guided through introducer 1030 and advanced along the posterior side of the posterior margin 1016 of SI joint 904 (outside the joint). Once probe 1040 is properly positioned, energy may be applied to create a lesion 1050 outside and/or within the joint (i.e. the lesion may or may not extend into the intra-articular space 1010 of the joint 904). In a further alternative of this treatment procedure, illustrated in FIG. 10*c*, introducer 1030 is manipulated until a tip 1032 of introducer 1030 enters intra-articular space 1010 at a more caudal point of the anterior-inferior margin 1020 of SI joint 904. Probe 1040 may then be guided through introducer 1030 and along the posterior side of the anterior margin 1022 of SI joint 904 (inside the joint). Once probe 1040 is properly positioned, energy may be applied to create a lesion 1050 along the anterior side of SI joint 904. In any of these embodiments, the introducer 1030 may be inserted some distance into the SI joint 904.

Referring now to the step of delivering energy through the probe(s), this may be accomplished by providing, for example, a generator, operable to deliver radiofrequency (RF) energy in the range of for example about 200 kHz to about 1 GHz, connecting the generator to the probe(s) and operating the generator to deliver said RF energy to the SI joint through an energy delivery device associated with a distal region of the probe(s). A generator that may be used to perform these treatment methods, by way of non-limiting example, is the Pain Management Generator (PMG) from Baylis Medical Company Inc., Montreal, QC, Canada. Features of this generator are described in co-pending U.S. patent application Ser. No. 10/122,413, filed on Apr. 16, 2002; Ser. No. 10/323,672, filed on Dec. 20, 2002; Ser. No. 10/864,410, filed on Jun. 10, 2004; Ser. No. 10/893,274, filed on Jul. 19, 2004; and Ser. No. 11/198,099, filed on Aug. 5, 2005. All of the aforementioned applications are incorporated herein by reference.

In one embodiment, the generator is operable to deliver sufficient energy to the target tissue through the probe(s) so that tissue within or adjacent to the SI joint may be ablated, as has been defined earlier. In such embodiments that involve the ablation of a region of tissue, the tissue ablated according to this aspect of the invention can include, but is not limited to, one or more of: neural tissue, whose ablation can prevent the transmission of pain sensation; structural or connective tissue, whose ablation can cause a contraction of collagen and a reduction in the volume of the intra-articular space of the joint; and vascular tissue, whose ablation may result in the disruption of nutrient supply to one or more neural structures. In some embodiments, as described above, energy may be delivered in a substantially homogeneous manner to create a substantially homogeneous lesion. In alternate embodiments, the energy delivered by the generator through the probe(s)

may not ablate tissue but may perform one or more other treatment functions, such as altering the structure of collagen (without causing cellular coagulation) or globally heating the joint, thereby altering the function of neural tissue, without necessarily ablating or destroying the nerves themselves. Thus, the function of neural tissue may be altered with or without ablating the neural tissue. Other alternative treatment functions may include, but are not limited to, denaturing enzymes or increasing heat shock proteins in the SI joint.

Alternatively, RF current, microwave current, or other energy could be delivered in a series of amplitude or frequency modulated pulses, whereby tissue heating is inhibited by interrupting periods of energy delivery with relatively long periods in which no energy is delivered. By pulsing the energy in this manner, a voltage that is sufficiently high to affect a prolonged disruption of the function of neural tissue may be used, while maintaining the tissue at a temperature such that no lesion will form, or such that the formation of a lesion will be inhibited. In further embodiments, a generator may not be used. In these embodiments, energy may be generated by a battery or any other means (in which case the entire system [probe and energy source] may be hand-held/portable/modular) and the invention is not limited in this regard. Without limitation, any delivery of energy that may result in a treatment effect to alleviate symptoms of SIJS is intended to be included within the scope of this aspect of the present invention.

Regarding connecting the generator to the probe(s), the generator may, in some embodiments, be releasably coupled to the probe(s). For example, this may be achieved by providing releasable electrical connectors at or close to the proximal region of the probe(s). In embodiments in which the probe(s) are cooled, the proximal region of the probe(s) may further comprise releasable connectors, such as Luer locks, to couple one or more means for cooling, such as peristaltic pumps and associated tubing, to the probe(s). In alternate embodiments, the probe(s) may be permanently attached to the generator and/or the one or more means for cooling.

As mentioned above, in some embodiments, the probe(s) may be operable to create a single strip lesion within the joint, for example a substantially homogeneous strip lesion. In addition, the probe(s) may be operable to create such a lesion during the course of a single energy delivery step or while the probe remains in a substantially static position, as has been described above. It should be noted, however, that creating strip lesions through one or more probe repositioning or energy delivery steps, as well as creating individual, non-strip lesions, also fall within the scope of this invention.

In addition, although the aforementioned embodiments have been described using only one probe, several probes may be used in order to deliver energy within the SI joint. Furthermore, each of these probes may comprise one or more conductive regions. For example, in alternate embodiments, two or more probes may be used in a bipolar configuration. In some such embodiments, the probes may, for example, be spaced apart by a distance that is not greater than about five times the diameter of the energy delivery devices located on the probes. Such spacing may be advantageous when using non-cooled probes. Using cooled probes, as discussed below, may allow for a larger separation distance between the probes. In addition, in some embodiments, the probes may be separated by a distance of at least about 1 cm. In other embodiments, probe separation may vary and may be more or less than the aforementioned maximum and minimum distances. In yet further embodiments, three or more probes may be used in a triphasic configuration. It should be noted that when more than one probe is used, the probes may be operated in a monopolar configuration and the invention is not limited in this regard. For example, several probes may be operated in a monopolar configuration, whereby a specific lesion shape may be obtained by determining an optimal spacing between probes that may produce a specific interference pattern and thus, a specific current density resulting in a desired lesion shape.

In some embodiments of this aspect of the present invention, the method may further comprise a step of moving the probe(s) to another location within the tissue if the user so desires. The probe(s) may be moved before, during, or after the step of delivering energy, and may be moved one or more times. The step of moving the probes may comprise one or more of the following actions: applying a force to bend the probe within the tissue (wherein the probe may thus be described as a 'steerable' probe), moving the probe intact within the tissue, removing the probe intact from the tissue, re-inserting the probe into the tissue and moving one or more parts of the probe (for example, extending or retracting a segmented probe telescopically) to move the position of one or more functional elements within the tissue.

In use, and with reference again to FIGS. 10a to 10c, a first embodiment of this aspect of a method of the present invention may be practiced as follows: a patient is made to lie prone on an operating table or similar structure, a grounding pad is placed on the surface of the patient's body and local anesthetic is provided in the area to be treated (for example, at or near the SI joint). If neural stimulation will be performed, as discussed below, the stimulation step may be performed prior to the delivery of anesthetic (if anesthetic is used). Prior to the insertion of the probe(s) or introducer(s), fluoroscopic imaging or other means may be used to visualize a patient's sacroiliac region in order to ascertain the desired approach for inserting the device(s) into the SI joint. This is particularly important with respect to SIJS treatment procedures because the anatomical structures involved may vary significantly from patient to patient. Various angles of approach and sites of entry may be used and the invention is not limited in this regard. After introducer 1030 has been inserted, the position of introducer 1030 may be verified using fluoroscopic imaging (or other imaging modalities) or other means, after is which probe 1040 may be inserted through a bore or lumen of introducer 1030 such that at least a portion of active portion 1042 of probe 1040 is located within or adjacent to joint 904, depending on the specific target lesion site. It should be noted that, in those embodiments that comprise a stylet to facilitate positioning of the probe, the stylet may be located within an introducer and may be removed from the introducer prior to insertion of the probe.

Figure 10:
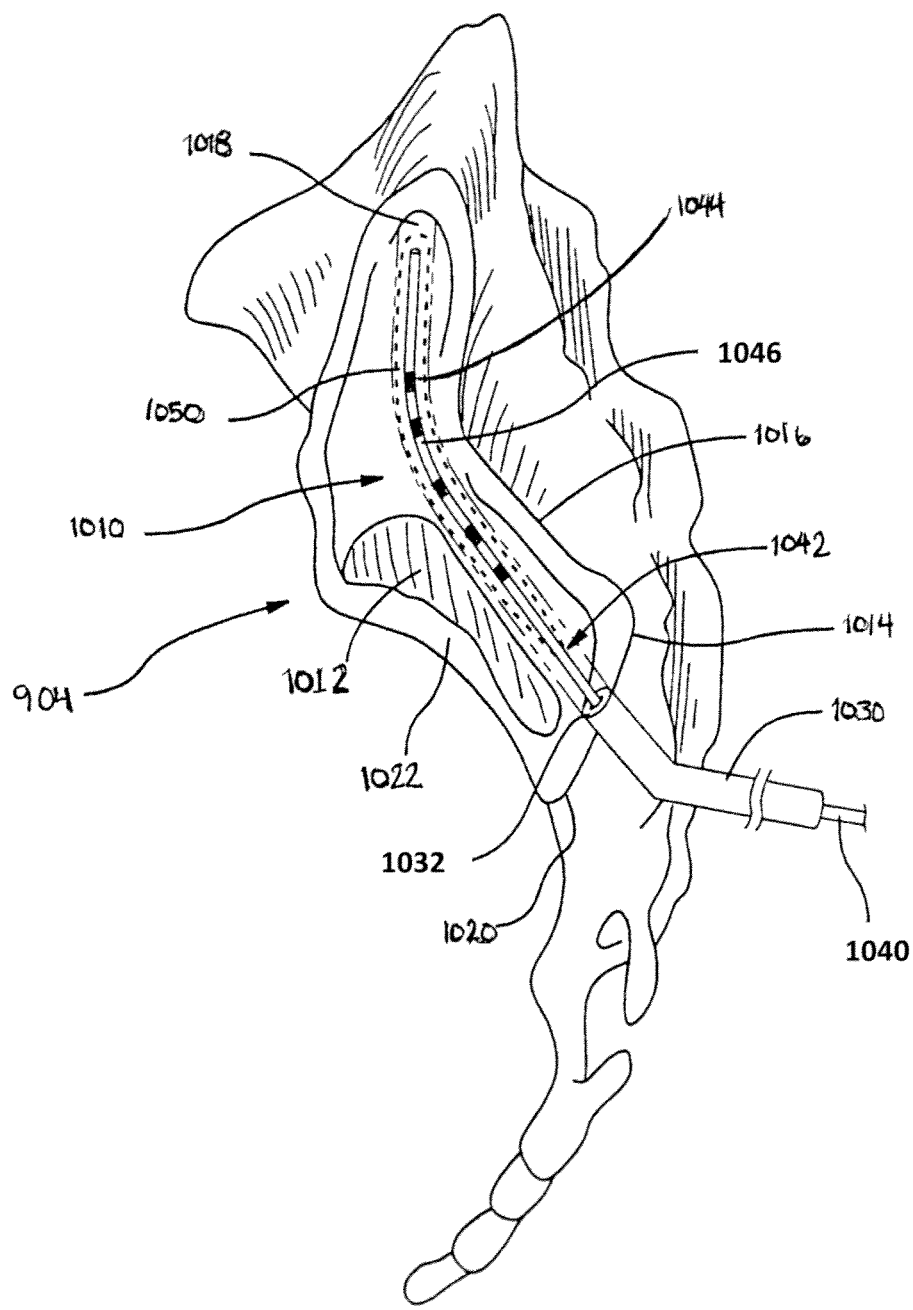
FIGS. 10A to 10C illustrate alternate embodiments of a method of the present invention.
Figure 10B:
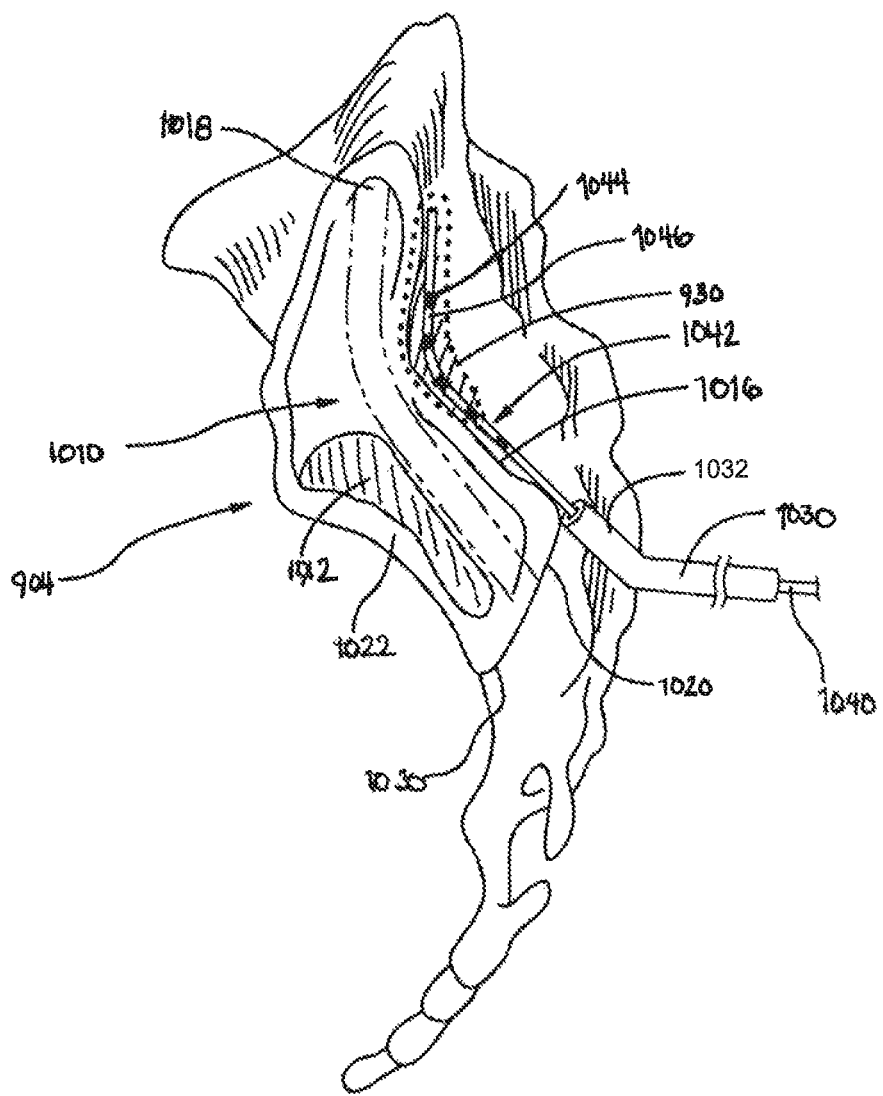
Figure 10C:
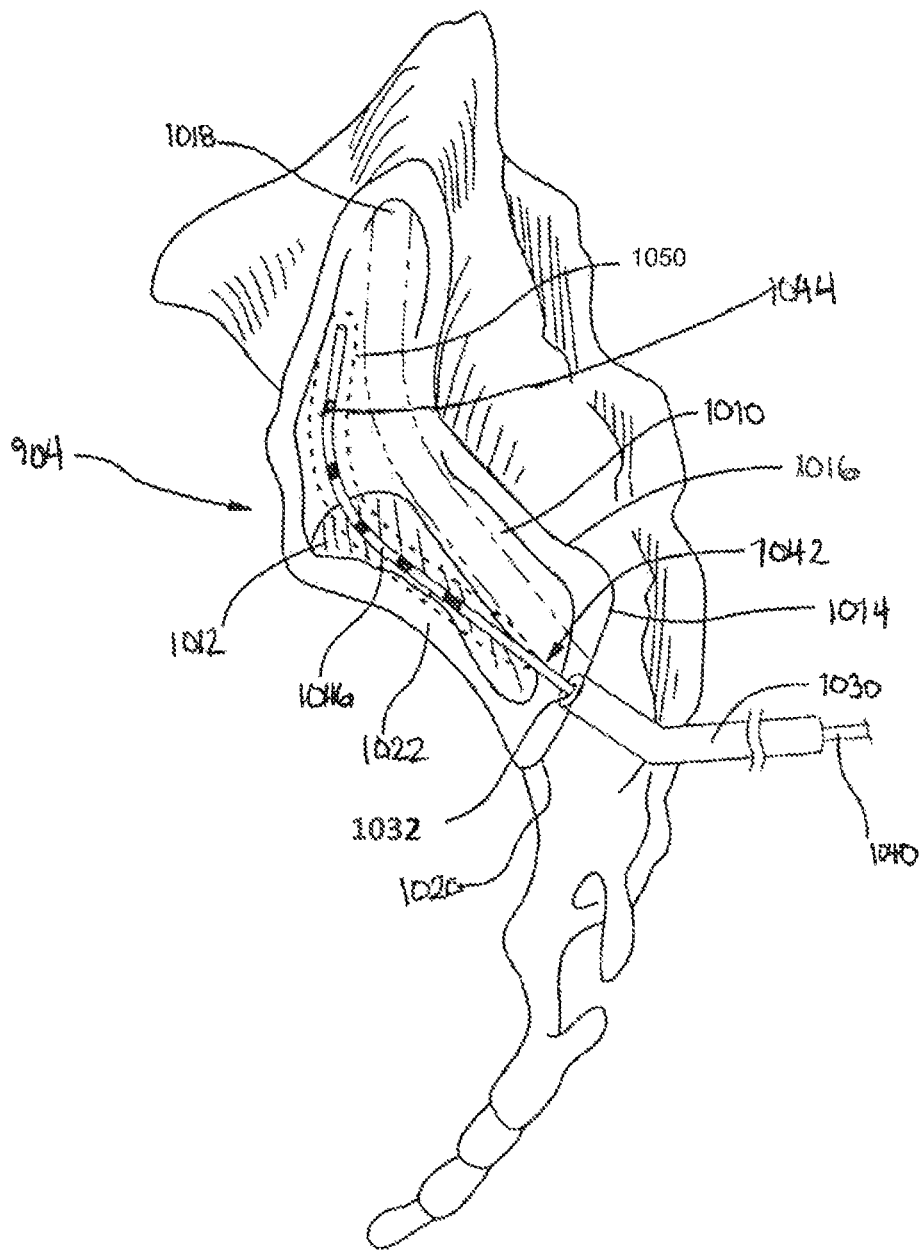

In some embodiments, as shown in FIG. 10a, probe 1040 is advanced far enough into joint 904 so that a strip lesion 1050, for example a substantially homogeneous strip lesion 1050, will be created across a substantial part of the long axis of joint 904 when energy is delivered to conductive regions 1046. Probe 1040 may be advanced until further advancement is impeded by an anatomical structure, such as a bone or a ligament. It may be desirable that probe 1040 be inserted into joint 904 in such a way so as to minimize damage to the connective tissues of the joint, including the articular cartilage located at the surfaces of the bones, as well as the various ligaments associated with joint 904. Therefore, in order to avoid damaging these tissues, the probe may be inserted into the cartilaginous space 1018 of joint 904, as shown in FIG. 10a, in which case it would be desirable to have a probe flexible enough to conform to the boundaries of cartilaginous space 1018. In addition, some embodiments may utilize a probe capable of creating a relatively thin strip lesion (i.e. a strip lesion with a small diameter or a strip lesion with short minor axes) so that the lesion does not extend too deeply into the cartilage. Depending on the specific probe that is used, a user may receive tactile feedback to indicate that the probe is contacting cartilage or ligamentous tissue and the user may then decide to retract the probe slightly and attempt to reposition the probe. In alternate embodiments, a probe may be introduced into the SI joint without being inserted into the cartilaginous space, for example in order to reach certain nerves which may be located throughout the joint, for example as shown in FIG. 10b.

In general, when inserting probe 1040 into joint 904, care should be taken to insert the probe as far as possible into joint 904 while minimizing the collateral damage to the tissues that make up the joint. In other embodiments, the probe may not initially extend a large distance into the joint, in which case smaller lesions may be made while advancing the probe slowly through the joint space in order to treat as much of the joint space as possible. In yet further embodiments, it may be desirable to have at least a portion of the probe located proximate to or within a region of cartilage. For example, this may be desirable if it is suspected that a fissure or other defect exists within the cartilage, in which case it may be beneficial to apply energy directly to the cartilage in order to heal the fissure or other defect. At this point, energy may be delivered from a generator via conductive regions 1046 to a target site within the tissue of SI joint 904. If the probe is steerable, the probe tip may be maneuvered into a second location within the joint and energy may again be delivered to ablate the neural tissue at the second location. This may be repeated as many times as the user wishes. If the probe is not steerable, the probe may be removed from the joint and/or the patient and the positioning and insertion steps may be repeated so that the probe is located at a second position, at which point energy may be delivered again at this location.

Once the user has determined that enough neural tissue has been ablated or otherwise affected, the introducer and probe may be removed from the body and the patient should be allowed to recover. It should be noted that this description is intended to be exemplary only and that other embodiments are envisioned as well. In addition, this invention is not intended to be limited by the number and type of probes used in this and other embodiments as well as the number and type of lesions created by these probes. It is also important to note that the aforementioned embodiments have been described with reference to a typical structure of an SI joint, as can be found in the literature. However, the SI joint is known to be extremely variable and the structures discussed with respect to this preferred embodiment may not be present in some individuals or may be located in different areas of the joint. Thus, the present invention is not intended to be limited by these embodiments.

In alternate embodiments of this aspect of the present invention, energy may be delivered in forms other than radiofrequency electrical energy, including but not limited to: other forms of electromagnetic energy, for example microwave energy or optical energy; thermal energy; mechanical energy; and ultrasonic energy; and combinations thereof. Additionally, the step of delivering energy could involve the use of other energy delivery devices including, but not limited to: microwave probes, optical fibers, resistive heaters, and ultrasound emitters.

The step of delivering energy to the tissue, may involve, in some embodiments, the use of devices in which the one or more probes are actively or passively cooled. Cooling of probes can prevent the searing or coagulation of tissue directly adjacent to the probe(s) and can prevent the vaporization of liquid within the tissue. Cooling can also be used to increase the maximum lesion volume that can be formed in a given tissue.

In addition to optionally measuring impedance, as in one embodiment described above, some embodiments further comprise an additional step of measuring the temperature of tissue at least at one location. This is generally desirable so as to ensure that a given region of tissue is not exceeding a certain temperature. For example, in some embodiments it may be desirable to maintain the temperature of tissue at or below a temperature required for neural ablation. A means for monitoring temperature may be located on or within or about a distal region of the one or more probes and the temperature of tissue located proximate to the distal region(s) of the probe (s) may be monitored using the means for monitoring temperature. Alternatively or in addition, a means for monitoring temperature may be located at a different location on the one or more probe(s) to monitor the temperature of a region of tissue located some distance away from the distal region(s) of the probe(s). Furthermore, one or more separate means for monitoring temperature may be inserted into the patient's body in order to monitor the temperature of one or more specific regions of tissue. The means for monitoring temperature may take the form of one or more thermocouples, thermistors, optical thermal sensors or any other means for monitoring or sensing temperature and the invention is not limited in this regard. The means for monitoring temperature may be connected directly to the energy source (e.g. the RF generator) or they may be monitored by an independent temperature monitoring device. These embodiments are intended to be exemplary only and are not intended to limit the present invention in any way.

As a feature of this aspect of the present invention, an embodiment of this method may further comprise one or more steps of modifying a treatment procedure in response to one or more measured parameters. These measured parameters may include, but are not limited to, temperature, position of the probe(s) or impedance. For example, if a temperature measurement is determined to be outside of a desired range, a treatment procedure may be modified by, for example, altering the amount of energy delivered by the generator (for example, by altering the maximum allowable temperature or changing the temperature ramp rate), modifying or modulating the one or more means for cooling in some way (for example, by adjusting the rate of coolant flow), or terminating the procedure. As another example, the amount of energy delivered by the generator may be modified based on the position of the one or more probes (for example, depending on the distance between a probe and the target treatment site or on the distance between the probes themselves when more than one probe is used). In such embodiments, a feedback system may be incorporated directly into the energy source so that any modification of a treatment procedure in response to a measured parameter may occur automatically. In other embodiments, there may not be an automatic feedback system in place, in which case a user may manually modify a treatment procedure in response to a measured parameter. In addition to modifying a treatment procedure based on measured parameters, this invention also provides for a step of determining the initial parameters to be used in a treatment procedure (for example, the initial maximum power level or tissue temperature, temperature ramp rate, etc.) using information that is known about the particular SI joint to be treated. For example, if pre-treatment testing reveals specific information about the SI is joint of a particular patient (this information may include, but is not limited to: joint geometry, presence or absence of synovial fluid, etc.), that information may be used to decide on what parameters to use initially for the treatment procedure.

In some embodiments of this aspect of the present invention, the step of performing a treatment, for example in order to reduce pain associated with SIJS, may comprise the addition or removal of material to or from the joint. Material that may be added to the joint includes, but is not limited to: alcohol, chemical lysing agents, pharmaceutical agents including, but not limited to, anesthetics and other medicaments, sealants, matrix molecules such as collagen or fibrinogen, electrolyte solutions, contrast media, or any combination of the above. Material that may be removed from the joint includes, but is not limited to: synovial fluid, ligamentous tissue, cartilage and any other material whose removal may help to treat the SI joint. The removal of material may be accomplished through various means, which can include aspiration, vaporization or mechanical conveyance. Furthermore, the steps of addition and removal of material can be performed concurrently, for example by irrigating the joint with a liquid medium while aspirating the liquid effluent from the space. The addition or removal of material may also be combined with the delivery of energy, as has described above, wherein the delivery of energy and the addition or removal of material may occur concurrently or sequentially. An exemplary device for removing material from a patient's body has been described in co-pending U.S. patent application Ser. No. 11/128,342, filed on May 13, 2005 as well as U.S. provisional patent application 60/594,109 filed on Mar. 11, 2005. These applications are herein incorporated by reference.

According to this aspect of the present invention, as has been described, one or more probes or other devices are placed at some location within or adjacent to the SI joint. It should be understood that the probe(s) may be inserted into any tissue within or adjacent to the joint, including, but not limited to the ligaments, cartilage or intra-articular region of the joint. Furthermore, as has already been mentioned, a probe may be inserted using any approach that allows access to the joint, including but not limited to: a superior posterior approach, an inferior posterior approach, or an anterior approach. For example, in one alternate embodiment, a probe may be inserted percutaneously using an inferior posterior approach and advanced into the SI joint through a synovial capsule 1012 located at or proximate to inferior margin 1014. In such embodiments, the probe may be operable to conform to the shape of synovial capsule 1012. In yet another embodiment, a probe and/or introducer may be inserted into a patient's body in such a manner so that the probe and/or introducer can be positioned proximate to the posterior margin of the SI joint, with the probe oriented approximately perpendicularly to the patient's body. In such an embodiment, the probe may be inserted into the joint and used to create a strip lesion along an anterior-posterior plane through the joint. Thus, this invention is not limited to one specific approach.

If more than one probe is used, the probes may be inserted into the joint using different approaches. For example, when practicing this method aspect of the present invention using two probes in a bipolar configuration, as has been previously mentioned, the probes may be inserted at a relatively higher angle (i.e. closer to an anterior-posterior plane approach) with respect to the patient's body. In such embodiments, the probes may not penetrate as far into the SI joint and may be more effective in treating the periphery of the SI joint, for example along the posterior joint line. In addition, when using probes in a bipolar configuration in this manner, it may be useful to follow a 'leapfrog' approach, wherein the two probes are inserted to initial locations and a lesion is created between the probes. Once the first lesion is created, the first probe is repositioned so as to be located on the other side of the second probe, for example more cephalad (towards the head, i.e. superior) in the joint, and a second lesion is created. Following this, the second probe is repositioned so as to be located on the other side of the first probe, even more cephalad in the joint, and so on. This procedure is repeated along the long axis of the joint until a sufficient portion of the joint has been treated. Depending on the specific case, this may occur after as few as one or two lesions are created or it may require treating the entire posterior margin of the joint, including in the area of the crest of the ilium. This method can also be practiced by using a multiplicity of probes and leaving each probe in place. In other words, once a probe is in place it may remain there and further probes may be inserted in order to achieve this 'leapfrog' lesioning approach. In this way, an effective strip lesion may be created. In other embodiments, bipolar probes may be used in conjunction with various other approaches and this invention is not limited to using bipolar probes with this specific approach.

In embodiments of the present invention that employ more than one probe, the probes used during the course of a treatment procedure may form part of the circuit of an electrical impedance meter, as is known in the art, wherein energy may be transmitted between the probes through a region of tissue, allowing a user to determine the impedance of said region of tissue. This feature may be useful to determine whether or not the impedance of the tissue lies within a 'normal' range—if the impedance of the tissue is found to be outside that range, it may be indicative of an injury or defect within the tissue. As mentioned above, a single probe may also have an impedance measuring capability, for example to help determine the location of the probe within a patient's body.

As an additional feature of this aspect of the present invention, certain embodiments may further comprise a step of performing a function to map the neural pathways in the tissue and this step may occur one or more times throughout the course of the procedure. The step of performing a function to map the neural pathways in the tissue can involve, in some embodiments, stimulation of the neural tissue at one or more physiological stimulation frequencies and subsequent observation to determine the effect of said stimulation. Various frequencies (for example, between about 1 and about 200 Hz) and voltages (for example, between about 0.1 to about 5 Volts) can be used to stimulate both sensory and motor nerves. Observation of said stimulation can take the form of visual, sensory, mechanical, or electrical detection of muscle activity, or the form of sensory or electrical detection of nociceptive or other sensory neural activity (e.g. temperature sensation). Using this step, it can be determined whether a target nerve or group of nerves has a function that would contraindicate its ablation or functional alteration. In some embodiments, the lack of a contraindication would lead to the step of delivering energy, whereas the presence of a contraindication would lead back to the step of inserting a probe or probes, whereby the step of inserting a probe or probes includes modifying the position of a probe or probes within the body. Furthermore, in some embodiments, a method of this aspect of the present invention may comprise a step of stimulating neural tissue after a treatment procedure in order to determine the effectiveness of the treatment procedure.

Other Applications

The present invention may be used in a wide range of treatment applications within the body, each of which may use a specific embodiment of a device of the present invention. Such applications include, but are not limited to: electrosurgical treatment of cardiac tissue, treatment of intervertebral discs, treatments of the facet joints of the spine, intraosseus treatment procedures, tumor treatments, prostate treatments and electrosurgical treatments of any other tissue. Such treatments may include but are not limited to ablation of neural tissue, ablation of vascular tissue, collagen shrinkage procedures, tissue coagulation, tissue vaporization and other procedures involving the delivery of energy or another treatment composition to a region of tissue.

In all applications using a device of the present invention, a method of using the device may generally involve the steps of inserting the device adjacent a tissue to be treated and delivering energy or another treatment composition to the tissue to be treated using an embodiment of a device of the present invention. Additional steps may include but are not limited to positioning a device using fluoroscopic imaging (or other medical imaging techniques such as CT, MRI and ultrasound) or other forms of guidance, repositioning the device where necessary, stimulating neural tissue by applying low-frequency energy, adjusting the electrical conductivity of the device, measuring an electrical or physiological parameter (e.g. tissue temperature, impedance, pressure, etc.) and adjusting an aspect of the treatment procedure based on the measured parameter.

The embodiments of the invention described above are intended to be exemplary only. The scope of the invention is therefore intended to be limited solely by the scope of the appended claims.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the some extent as if each individual publication, patent or patent application was specifically and individually indicated to be incorporated herein by reference. In addition, citation or identification of any reference in this application shall not be construed as an admission that such reference is available as prior art to the present invention.

We claim:

1. A method of treating the sacroiliac region of a patient's body by delivering energy, comprising the steps of:
   providing a probe having an active portion at a distal end thereof, the active portion having at least two regions of electrical discontinuity which result in a region of increased current density about the probe when energy is delivered to the probe, the active portion slidably disposed within an insulating member such that a position of the active portion relative to the insulating member may be altered;
   inserting the probe into a patient's body proximate a sacrum and positioning the probe at a target site external to a sacroiliac joint;
   delivering energy to the probe to treat tissue within the target site; and
   moving the insulating member along a length of the active portion during the step of delivering energy such that a position of at least one of the regions of electrical discontinuity is adjusted, wherein the active portion of the probe creates a strip lesion during a single energy delivery step.

2. The method of claim 1, wherein energy is delivered to the target site to create a substantially homogeneous lesion.

3. The method of claim 2, wherein an active portion of the probe is at least 10 mm in length.

4. The method of claim 3, wherein the active portion of the probe is at least 15 mm in length.

5. The method of claim 1, wherein energy is delivered in a monopolar configuration.

6. The method of claim 1, wherein energy is delivered in a bipolar configuration.

7. The method of claim 1, wherein the step of delivering energy comprises delivering electrical energy selected from the group consisting of radiofrequency current and microwave current.

8. The method of claim 1, wherein energy is delivered in order to reduce one or more symptoms of sacroiliac joint syndrome.

9. The method of claim 1, wherein energy is delivered in order to ablate one or more neural structures.

10. The method of claim 1, wherein the target site comprises at least a portion of a sacral neural crescent.

11. The method of claim 10, wherein the energy is delivered to treat at least two branches of a sacral nerve.

12. The method of claim 10, further comprising the steps of repositioning the probe at another sacral neural crescent and delivering energy to treat tissue within the other sacral neural crescent.

13. The method of claim 1, wherein the active portion has at least three of the regions of electrical discontinuity.

14. The method of claim 13, wherein the at least three regions of electrical discontinuity include at least three electrically conductive and exposed regions separated by electrically insulated regions and wherein the lengths of at least two of the conductive regions differ along a line extending between a proximal end and a distal end of the probe.

15. The method of claim 14, wherein one of the conductive regions towards the middle of the active portion has a length less than another of the conductive portions located away from the middle of the active portion along the line extending between the proximal end and the distal end of the probe.

16. The method of claim 1, wherein the probe is inserted towards an inferior portion of the sacrum and wherein the step of positioning the probe comprises advancing the probe in a cephalad direction substantially along the sacrum.

17. The method of claim 16, wherein advancement of the probe substantially follows a curve of a sacrum.

18. The method of claim 1, wherein the step of delivering energy comprises delivering energy to treat nerves exiting from at least two foraminal apertures in a single continuous period of energy delivery.

19. The method of claim 17, wherein the probe is positioned lateral to sacral foramen and medial to the sacroiliac joint.

20. The method of claim 19, wherein the probe is advanced until a superior aspect of the sacrum.

21. The method of claim 1, wherein the step of delivering energy comprises delivering energy to create a lesion substantially along a caudal-cranial axis of the patient's body.

22. A method of treating the sacroiliac region of a patient's body comprising the step of delivering energy to a sacral neural crescent to create a substantially homogeneous lesion to ablate at least two branches of sacral nerve passing through the sacral neural crescent while the probe remains in a substantially static position.

* * * * *